US008486626B2

(12) United States Patent
Umansky et al.

(10) Patent No.: US 8,486,626 B2
(45) Date of Patent: Jul. 16, 2013

(54) METHODS OF DETECTING CELL-FREE MIRNA IN URINE AND BLOOD

(75) Inventors: Samuil R. Umansky, Princeton, NJ (US); Hovsep S. Melkonyan, Princeton, NJ (US); Vladimir S. Scheinker, Congers, NY (US)

(73) Assignee: Trovagene, Inc., San Diego, CA (US)

( * ) Notice: Subject to any disclaimer, the term of this patent is extended or adjusted under 35 U.S.C. 154(b) by 285 days.

(21) Appl. No.: 12/229,378

(22) Filed: Aug. 22, 2008

(65) Prior Publication Data
US 2009/0081640 A1 Mar. 26, 2009

Related U.S. Application Data

(60) Provisional application No. 60/965,871, filed on Aug. 22, 2007.

(51) Int. Cl.
*C12Q 1/68* (2006.01)
*C07H 21/02* (2006.01)

(52) U.S. Cl.
USPC .......... 435/6.1; 536/24.5; 435/6.11; 435/6.12

(58) Field of Classification Search
None
See application file for complete search history.

(56) References Cited

U.S. PATENT DOCUMENTS

| | | | |
|---|---|---|---|
| 5,168,039 A | 12/1992 | Crawford et al. | |
| 5,631,130 A | 5/1997 | Leckie et al. | |
| 5,712,385 A | 1/1998 | McDonough et al. | |
| 5,731,150 A | 3/1998 | Sandhu et al. | |
| 5,770,366 A | 6/1998 | Bogdahn et al. | |
| 5,808,041 A | 9/1998 | Padhye et al. | |
| 6,020,124 A | 2/2000 | Sorenson | |
| 6,251,638 B1 * | 6/2001 | Umansky et al. | 435/91.2 |
| 6,287,820 B1 | 9/2001 | Umansky et al. | |
| 6,368,800 B1 | 4/2002 | Smith et al. | |
| 6,492,144 B1 | 12/2002 | Umansky et al. | |
| 7,803,929 B2 | 9/2010 | Melkonyan et al. | |
| 2002/0119478 A1 | 8/2002 | Umansky et al. | |
| 2003/0152591 A1 | 8/2003 | Sablon et al. | |
| 2003/0152982 A1 | 8/2003 | De Beenhouwer et al. | |
| 2004/0053264 A1 | 3/2004 | Park | |
| 2006/0183108 A1 | 8/2006 | Melkonyan et al. | |
| 2006/0292616 A1 * | 12/2006 | Neely et al. | 435/6 |
| 2007/0037181 A1 | 2/2007 | Melkonyan et al. | |
| 2007/0161004 A1 * | 7/2007 | Brown et al. | 435/6 |
| 2007/0202511 A1 * | 8/2007 | Chen et al. | 435/6 |
| 2010/0068711 A1 | 3/2010 | Umansky et al. | |

FOREIGN PATENT DOCUMENTS

| | | |
|---|---|---|
| WO | WO-95/04140 A1 | 2/1995 |
| WO | WO-98/54364 A1 | 12/1998 |
| WO | WO-98/58086 A2 | 12/1998 |
| WO | WO-2006/088895 A2 | 8/2006 |
| WO | WO-2006/089203 A2 | 8/2006 |

OTHER PUBLICATIONS

Bryzgunova et al (Ann. N.Y. Acad. Sci 1075: 334-340, 2006).*
http://www.ambion.com/catalog/CatNum.php?1931 Oct. 18, 2006.*
Cai et al (PLoS Pathogens 2(3): e23, 0239-0247, 2006).*
Kim et al (J. Clin. Invest. 1998. 102:1815-1823).*
Wong et al (Clinical Chemistry 51:10 1786-1795 (2005)).*
Wong et al (Clin Cancer Res 2006;12:2512-2516).*
Amacher, et al., Regulatory Toxicology and Pharmacology 27:119-130 (1998).
Ameisen Cell Death Differ., 11:4-10 (2004).
Arends et al., American Journal of Pathology, 136:593-608(1990).
Beuvink et al., J. Nucleic Acids Res., 35:1-11, e52 (2007).
Bischoff et al., Human Reproduction Update, 8:493-500 (2002).
Botezatu et al., Clin Chem., 46:1078-1084,(2000).
Bredesen et al., Stroke, 38(2 Suppl):652-660 (2007).
Chang et al., Annu. Rev. Genomics Hum. Genet., 8:215-239 (2007).
Chen et al., Nature Genetics, 38:228-233 (2006).
Chim et al., Clinical Chemistry, 54:482-490 (2008).
Doty et al., Proc. Natl. Acad. Sci., USA 46:461-476 (1960).
Fleischhacker et al., Biochimica et Biophysica Acta, 1775:181-232 (2007).
Jay et al., DNA and Cell Biology., 26:293-300 (2007).
Kerr et al., Br. J. Cancer, 26, 239-257 (1972).
Kroemer, et al., Cell Death and Differentiation, 12:1463-1467 (2005).
Lagos-Quintana et al., Current Biology, 12:735-739 (2002).
Lawrie et al., British Journal of Haematology, 141:672-675 (2008).
Liang et al., BMC Genomics, 8:166 (2007).
Lichtenstein et al., Annals New York Academy of Sciences, 945:239-249 (2001).
Lo Y.M. Annals New York Academy of Sciences, 945:1-7 (2001).
Lockshin et al. Int J Biochem Cell Biol., 36:2405-2419 (2004).
Lu et al., Nature, 435:834-838 (2005).
Lukiw et al, NeuroReport, 18:297-300 (2007).
Mair et al., Clin Chem Lab Med., 37:1077-1084 (1999).
Marmur and Lane, Proc. Natl. Acad. Sci. USA, 46:453-461 (1960).
Melkonyan et al., Annals New York Academy of Sciences, 1137:73-81 (2008).
Mitchell et al., Proceedings of the National Academy of Sciences USA, 105:10513-10518 (2008).
Negrini et al., Journal of Cell Science, 120:1833-1840 (2007).
Nelson et al., Neuropathol. Exp. Neurol., 66:461-468 (2007).
Nunes et al., Rev,. Port. Cardiol., 20:785-788 (2001).
Oh S et al., Curr Gastroenterol Rep., 3:12-18 (2001).
Rochling et al. Clinical Cornerstone, 3:1-12 (2001).
Salaspuro, et al., Enzyme., 37:87-107 (1987).
Su et al., Annals of the New York Academy of Sciences, 1022:81-89(2004).

(Continued)

Primary Examiner — Richard Schnizer
(74) Attorney, Agent, or Firm — Patentique PLLC

(57) ABSTRACT

Described are non-invasive methods of detecting in vivo cell death by measuring levels of ubiquitous and tissue specific miRNA. The method can be applied for detection of pathologies caused or accompanied by cell death, as well as for diagnosis of infectious disease, cytotoxic effects induced by different chemical or physical factors, and the presence of specific fetal abnormalities.

17 Claims, 17 Drawing Sheets

OTHER PUBLICATIONS

Su et al., Journal of Molecular Diagnostics, 6:101-107 (2004).
Swarup et al., FEBS Letters, 581:795-799 (2007).
Taback et al., Current Opinion in Molecular Therapeutics, 6:273-278 (2004).
Tong et al., Clinica Chimica Acta, 363:187-196 (2006).
Umansky et al., Advances in Pharmacology., 41:383-407 (1997).
Umansky et al., Biochim Biophys Acta., 655, 9-17 (1981).
Umansky, J. Theor. Biol., 97:591-602 (1982).
Visone R., et al. Oncogene, 26:7590-7595 (2007).
International Search Report for PCT/US2008/009991, mailed Mar. 18, 2009.
Aceti et al., "Identification of HIV patients with active pulmonary tuberculosis using urine based polymerase chain reaction assay", *Thorax.*, 54:145-146 (1999).
Achtman et al., "Recombination and clonal groupings within *Helicobacter pylori* from different geographical regions", *Mol. Microbiol.*, 32:459-470 (1999).
Ahern, H., "Biochemical, Reagent Kits Offer Scientists Good Return on Investment", *Scientist*, 9:20-24 (1995).
Akopyanz et al., "DNA diversity among clinical isolates of *Helicobacter pylori* detected by PCR-based RAPD fingerprinting", *Nucl. Acids Res.*, 20(19):5137-5142 (1992).
Al-Yatama et al., "Detection of Y chromosome-specific DNA in the plasma and urine of pregnant women using nested polymerase chain reaction", *Prenatal Diagnosis*, 21:399-402 (2001).
Alm et al., "Genomic-sequence comparison of two unrelated isolates of the human gastric pathogen *Helicobacter pylori*", *Nature*, 397:176-180 (1999).
Atherton et al., "Vacuolating Cytotoxin (*vacA*) Alleles of *Helicobacter pylori* Comprise Two Geographically Widespread Types, m1 and m2, and Have Evolved Through Limited Recombination", *Curr. Microbiol.*, 39:211-218 (1999).
Atherton, J. C., "The clinical relevance of strain types of *Helicobacter pylori*", *Gut*, 40:701-703 (1997).
Axon, A. T. R., "Are all helicobacters equal? Mechanisms of gastroduodenal pathology and their clinical implications", *Gut*, 45(Supp. 1):11-14 (1999).
Barany, F., "Genetic disease detection and DNA amplification using cloned thermostable ligase", *Proc. Natl. Acad. Sci. USA*, 88:189-193 (1991).
Bedi et al., "Association of BK virus with failure of prophylaxis against hemorrhagic cystitis following bone marrow transplantation", *J. Clin. Oncol.*, 13(5):1103-1109 (1995).
Bekkaoui et al., "Cycling Probe Technology with RNase H Attached to an Oligonucleotide", *BioTech.*, 20:240-248 (1996).
Belli et al., "Simplified Polymerase Chain Reaction Detection of New World *Leishmania* in Clinical Specimens of Cutaneous Leishmaniasis", *Am. J. Tropical Med. Hygiene*, 58(1):102-109 (1998).
Bickley et al., "Evaluation of the polymerase chain reaction for detecting the urease C gene of *Helicobacter pylori* in gastric biopsy samples and dental plaque", *J. Med. Microbiol.*, 39:338-344 (1993).
Blackwood et al., "Reassessment of Sequence-Based Targets for Identification of *Bacillus* Species", *J. Clin. Microbiol.*, 42:1626-1630 (2004).
Blaser et al., "Infection with *Helicobacter pylori* Strains Possessing *cagA* is Associated with an Increased Risk of Developing Adenocarcinoma of the Stomach", *Cancer Res.*, 55:2111-2115 (1995).
Botezatu et al., "Genetic Analysis of DNA Excreted in Urine: A New Approach for Detecting Specific Genomic DNA Sequences from Cells Dying in an Organism", *Clin. Chem.*, 46(8):1078-1084 (2000).
Broccolo et al., "Rapid Diagnosis of Mycobacterial Infections and Quantitation of *Mycobacterium tuberculosis* Load by Two Real-Time Calibrated PCR Assays", *J. Clin. Microbiol.*, 41(10):4565-4572 (2003).
Buffone et al., "Improved Amplification of Cytomegalovirus DNA from Urine after Purification of DNA with Glass Beads", *Clin. Chem.*, 37(11):1945-1949 (1991).
Chan et al., "Association between polyomaviruria and microscopic haematuria in bone marrow transplant recipients", *J. Infection*, 29:139-146 (1994).
Chan et al., "Molecular Characterization of Circulating EBV DNA in the Plasma of Nasopharyngeal Carcinoma and Lymphoma Patients", *Cancer Res.*, 63:2028-2032 (2003).
Clayton et al., "Sensitive Detection of *Helicobacter pylori* by Using Polymerase Chain Reaction", *J. Clin. Microbiol.*, 30(1):192-200 (1992).
Cover et al., "Divergence of Genetic Sequences for the Vacuolating Cytotoxin among *Helicobacter pylori* Strains", *J. Biol. Chem.*, 269(14):10566-10573 (1994).
de Araujo et al., "A retrospective survey of dengue virus infection in fatal cases from an epidemic in Brazil", *J. Virological Meth.*, 155:34-38 (2009).
Del Portillo et al., "Amplification of a Species-Specific DNA Fragment of *Mycobacterium tuberculosis* and Its Possible Use in Diagnosis", *J. Clin. Microbiol.*, 29(10):2163-2168 (1991).
Designer PCT™ from Research Genetics, *Nucl. Acids Res.*, 22(15) (Aug. 11, 1994).
DIALOG computer database search, "Literature regarding bladder cancer diagnosis through urinalysis," (1996).
Disch et al., "Detection of circulating *Leishmania chagasi* DNA for the non-invasive diagnosis of human infection", *Trans. Royal Soc. Tropical Med. Hygiene*, 97:391-395 (2003).
Disch et al., "Rapid clearance of circulating *Leishmania* kinetoplast DNA after treatment of visceral leishmaniasis", *Acta Tropica*, 92:279-283 (2004).
Drago et al., "Real-Time PCR Assay Rapid Detection of *Bacillus anthracis* Spores in Clinical Samples", *J. Clin. Microbiol.*, 40(11):4399 (2002).
Drobniewski et al., "Modern laboratory diagnosis of tuberculosis", *Lancet Infectious Diseases*, 3:141-147 (2003).
Echavarria et al., "PCR Method for Detection of Adenovirus in Urine of Healthy and Human Immunodeficiency Virus-Infected Indivduals", *J. Clin. Microbiol.*, 36(11):3323-3326 (1998).
Elzinga et al., "Scale up: meeting targets in global tuberculosis control", *Lancet*, 363:814-819 (2004).
Fasanella et al., "Detection of anthrax vaccine virulence factors by polymerase chain reaction", *Vaccine*, 19:4214-4218 (2001).
Fenves, A. Z., "Legionnaires' disease associated with acute renal failure: a report of two cases and review of the literature", *Clin. Nephrology*, 23:96-100 (1985).
Frazier et al., "DNA Probes for Detecting *Coxiella burnetii* Strains", *Acta Virol.*, 36:83-89 (1992).
Friedlander, A. M., "DNA Release as a Direct Measure of Microbial Killing by Phagocytes", *Infect. Immunity*, 22(1):148-154 (1978).
Gal et al., "Detection of *Plasmodium falcipaurm* DNA in Plasma", *Ann. N.Y. Acad. Sci.*, 945:234-238 (2001).
Goman et al., "The complete sequence of a *Plasmodium malariae* SSUrRNA gene and its comparison to other plasmodial SSUrRNA genes", *Mol. Biochem. Parasitol.*, 45:281-288 (1991).
Green et al., "Demonstration of a Capsule Plasmid in *Bacillus anthracis*", *Infect. Immunity*, 49(2):291-297 (1985).
Haines et al., "Interstitial nephritis in a patient with legionnaires' disease", *Postgraduate Medicine*, 81(3):77-79 (1987).
Hammer et al., "Rapid Detection of *Helicobacter pylori* in Gastric Biopsy Material by Polymerase Chain Reaction", *J. Clin. Microbiol.*, 30(1):54-58 (1992).
Hemal et al., "Polymerase Chain Reaction in Clinically Suspected Genitourinary Tuberculosis: Comparison with Intravenous Urography, Bladder Biopsy, and Urine Acid Fast Bacilli Culture", *Urology*, 56:570-574 (2000).
Higgins et al., "A Field Investigation of *Bacillus anthracis* Contamination of U.S. Department of Agriculture and Other Washington, D.C., Buildings during the Anthrax Attack of Oct. 2001", *Applied Environ. Microbiol.*, 69(1):593-599 (2003).
Ho et al., "Direct Molecular Detection of Nucleic Acids by Fluorescence Signal Amplification", *J. Am. Chem. Soc.*, 127:12673-12676 (2005).
Ho et al., "Direct Polymerase Chain Reaction Test for Detection of *Helicobacter pylori* in Humans and Animals", *J. Clin. Microbiol.*, 29:2543-2549 (1991).

Hurtle et al., "Detection of the *Bacillus anthracis gyrA* Gene by Using a Minor Groove Binder Probe", *J. Clin. Microbiol.*, 42:179-185 (2004).
Jeong et al., "Genotyping of the JC Virus in Urine Samples of Healthy Korean Individuals", *J. Med. Virol.*, 72:281-289 (2004).
Kafwabulula et al., "Evaluation of PCR-based methods for the diagnosis of tuberculosis by identification of mycobacterial DNA in urine samples", *Int. J. Tuberc. Lung Dis.*, 6(8):732-737 (2002).
Keim et al., "Multiple-Locus Variable-Number Tandem Repeat Analysis Reveals Genetic Relationships within *Bacillus anthracis*", *J. Bacteriol.*, 182:2928-2936 (2000).
Kleanthous et al., "Characterization of a plasmid from *Helicobacter pylori* encoding a replication protein common to plasmids in Gram-positive bacteria", *Mol. Microbiol.*, 5(10):2377-2389 (1991).
Kogan et al., "An improved method for prenatal diagnosis of genetic diseases of analysis of amplified DNA sequences", *N.E. J. Med.*, 317(16): 985-990 (1987).
Koide et al., "Fragmentation of cell-free fetal DNA in plasma and urine of pregnant women", *Prenatal Diagnosis*, 25:604-607 (2005).
Kolk et al., "Detection of *Mycobacterium tuberculosis* in Clinical Samples by Using Polymerase Chain Reaction and a Nonradioactive Detection System", *J. Clin. Microbiol.*, 30:2567-2575 (1992).
Kox et al., "Early diagnosis of tuberculous meningitis by polymerase chain reaction", *Neurol.*, 45:2228-2232 (1995).
Lee et al., "Programmed cell death in the unicellular protozoan parasite *Leishmania*", *Cell Death Different.*, 9:53-64 (2002).
Leppla, S. H., "Anthrax Toxins", in *Handbook of Natural Toxins.*, Natl. Inst. Dental Res., Natl. Inst. Health, Bethesda, Maryland, Ch. 23, pp. 543-572 (1995).
Li et al., "HIV-1 DNA proviral sequences in fresh urine pellets from HIV-1 seropositive persons", *Lancet*, 335:1590-1591 (1990).
Lisby et al., "Polymerase chain reaction as a rapid diagnostic assay for cytomegalovirus infection in renal transplant patients", *APMIS*, 102:690-694 (1994).
Lo et al., "Detection of single-copy fetal DNA sequence from maternal blood", *Lancet*, 335:1463-1464 (1990).
Lo et al., "Prenatal sex determination by DNA amplification from maternal peripheral blood", *Lancet*, 2:1363-1365 (1989).
Lo et al., Prenatal sex determination from maternal peripheral blood using the polymerase chain reaction, *Human Genet.*, 90:483-488 (1993).
Lo, Y. M. D., "Molecular Testing of Urine: Catching DNA on the Way Out", *Clin. Chem.*, 46:1039-1040 (2000).
Logan et al., "*Bacillus* and Other Aerobic Endospore-Forming Bacteria", in *Manual of Clinical Microbiology*, 8th Ed, Murray et al., eds., ASM Press, Washington DC, Ch. 32, pp. 445-460 (2004).
Lu et al., "Comparison of Five PCR Methods for Detection of *Helicobacter pylori* DNA in Gastric Tissues", *J. Clin. Microbiol.*, 37:772-774 (1999).
Maiwald et al., "Detection of *Legionella* DNA in Human and Guinea Pig Urine Samples by the Polymerase Chain Reaction", *Eur. J. Clin. Microbiol. Infect. Diseases*, 14(1):25-33 (1995).
Maiwald et al., "Evaluation of the Detection of *Borrelia burgdorferi* DNA in Urine Samples by Polymerase Chain Reaction", *Infection*, 23(3):173-179 (1995).
Mao et al., "Microsatellite alterations as clonal markers for the detection of human cancer", *Proc. Natl. Acad. Sci. USA*, 91:9871-9875 (1994).
Mao et al., "Molecular Detection of Primary Bladder Cancer by Microsatellite Analysis", *Science*, 271:659-662 (1996).
Marei et al., "Evaluation of a rapid bacteriophage-based method for the detection of *Mycobacterium tuberculosis* in cilnical samples", *J. Med. Microbiol.*, 52:331-335 (2003).
McCutchan et al., "Primary sequences of two small subunit ribosomal RNA genes from *Plasmodium falciparum*", *Mol. Biochem. Parasitol.*, 28:63-68 (1988).
MEDLINE patent database search, "Genetic testing of DNA from urine," (1996) 30 pages.
Mercier et al., "Detection of *Borrelia burgdorferi* DNA by polymerase chain reaction in urine specimens of patients with erythema migrans lesions", *Mol. Cell. Probes*, 11:89-94 (1997).
Mikesell et al., "Plasmids, Pasteur, and Anthrax", *ASM News*, 49:320-322 (2002).

Mobley, H. L. T., "Defining *Helicobacter pylori* as a Pathogen: Strain Heterogeneity and Virulence", *Am. J. Med.*, 100:(Supp. 5A):2S-11S (1996).
Moussa et al., "Rapid Diagnosis of Genitourinary Tuberculosis by Polymerase Chain Reaction and Non-Radioactive DNA Hybridization", *J. Urol.*, 164:584-588 (2000).
Mukopadhyay et al., "A structural perspective on the *flavivirus* life cycle", *Nat. Rev. Microbiol.*, 3(1):13-22 (2005).
Murdoch et al., "Use of the Polymerase Chain Reaction to Detect *Legionella* DNA in Urine and Serum Samples from Patients with Pneumonia", *Clin. Infect. Diseases*, 23:475-480 (1996).
Nakahori et al., "A human Y-chromosome specific repeated DNA family (DYZ1) consists of a tandem array of pentanucleotides", *Nucl. Acids Res.*, 14(19):7569-7580 (1986).
Navarre et al., "Pathogen-induced apoptosis of macrophages: a common end for different pathogenic strategies", *Cell. Microbiol.*, 2(4):265-273 (2000).
Nickeleit et al., "Polyomavirus Infection of Renal Allograft Recipients: From Latent Infection to Manifest Disease", *J. Am. Soc. Nephrol.*, 10(5):1-12 (1999).
Oggioni et al., "Protocol for Real-Time PCR Identification of Anthrax Spores from Nasal Swabs after Broth Enrichment", *J. Clin. Microbiol.*, 40:3956-3963 (2002).
Piersimoni et al., "Performance Assessment of Two Commercial Amplification Assays for Direct Detection of *Mycobacterium tuberculosis* Complex from Respiratory and Extrapulmonary Specimens", *J Clin. Microbiol.*, 40(11):4138-4142 (2002).
Piersimoni et al., "Relevance of Commercial Amplification Methods for Direct Detection of *Mycobacterium tuberculosis* Complex in Clinical Samples", *J. Clin. Microbiol.*, 41(12):5355-5365 (2003).
Poloni et al., "Detection of dengue virus in saliva and urine by real time RT-PCT", *Vir. J.*, 7(22):1-4 (2010).
Pornthanakasem et al., "Human papillomavirus DNA in plasma of patients with cervical cancer", *BMC Cancer*, 1:2 (2001) 8 pages.
Poulter et al., "Acute interstitial nephritis complicating Legionaires' Disease", *Clin. Nephrol.*, 15(4):216-220 (1981).
Prosch et al., "Monitoring of Patients for Cytomegalovirus After Organ Transplantation by Centrifugation Culture and PCR", *J. Med. Virol.*, 38:246-251 (1992).
Qari et al., "Phylogenetic Relationship among the Malaria Parasites Based on Small Subunit rRNA Gene Sequences: Monophyletic Nature of the Human Malaria Parasite, *Plasmodium falciparum*", *Mol. Phylogenetics Evolution*, 6:157-165 (1996).
Qi et al., "Biological characteristics of dengue virus and potential targets for drug design", *Acta Biochim. Biophys. Sin.*, 40(2):91-101 (2008).
Qi et al., "Utilization of the *rpoB* Gene as a Specific Chromosomal Marker for Real-Time PCR Detection of *Bacillus anthracis*", *Appl. Environ. Microbiol.*, 67(8):3720-3727 (2001).
Sarmiento et al., "Assessment by Meta-Analysis of PCR for Diagnosis of Smear-Negative Pulmonary Tuberculosis", *J. Clin. Microbiol.*, 41(7):3233-3240 (2003).
Schatzl et al., "Detection by PCR of Human Polyomaviruses BK and JC in Immunocompromised Individuals and Partial Sequencing of Control Regions", *J. Med. Virol.*, 42:138-145 (1994).
Schurmann et al., "Pulmonary and Extrapulmonary Manifestations of *L. pneumophila*", *Zbl. Bakt. Hyg., I. Abt. Orig. A.*, 255:120-126 (1983).
Seah et al., "Semi-nested PCR using NS3 primers for the detection and typing of dengue viruses in clinical serum specimens", *Clin. Diagnostic Virol.*, 4:113-120 (1995).
Sechi et al., "Detection of *Mycobacterium tuberculosis* by PCR analysis of urine and other clinical samples from AIDS and non-HIV-infected patients", *Mol. Cell. Probes*, 11:281-285 (1997).
Shilo et al., "DNA sequences homologous to vertebrate oncogenes are conserved in *Drosophila melanogaster*", *Proc. Natl. Acad. Sci. USA*, 78(11):6789-6792 (1981).
Su et al., "Human Urine Contains Small, 150 to 250 Nucleotide-Sized, Soluble DNA Derived from the Circulation and May Be Useful in the Detection of Colorectal Cancer", *J. Mol. Diagnostics*, 6(2):101-107 (2004).
Su et al., "Transrenal DNA as a Diagnostic Tool", *Ann. N.Y. Acad. Sci.*, 1022:81-89 (2004).

Tamarit et al., "Human cytomegalovirus (HCMV)-specific CD4+ T lymphocyte response in AIDS patients with no past or current HCMV disease following HAART", *J. Clin. Virol*., 29:308-314 (2004).
Tomb et al., "The complete genome sequence of the gastric pathogen*Helicobacter pylori", Nature*, 388:539-547 (1997).
Torrea et al., "PCR-based detection of the *Mycobacterium tuberculosis* complex in urine of HIV-infected and uninfected pulmonary and extrapulmonary tuberculosis patients in Burkina Faso", *J. Med. Microbiol*., 54:39-44 (2005).
Tummuru et al., "Cloning and Expression of a High-Molecular-Mass Major Antigen of *Helicobacter pylori*: Evidence of Linkage to Cytotoxin Production", *Infect. Immunity*, 61(5):1799-1809 (1993).
Uchida et al., "Virulence and Immunogenicity in Experimental Animals of *Bacillus anthracis* Strains Harbouring or Lacking 110 MDa and 60 MDa Plasmids", *J. Gen. Microbiol*., 132:557-559 (1986).
Umansky et al., "In vivo DNA Degradation in Thymocytes of γ-Irradiated or Hydrocortisone-Treated Rats", *Biochim. Biophys. Acta*, 655:9-17 (1981).
Utting et al., "Microsatellite Analysis of Free Tumor DNA in Urine, Serum, and Plasma of Patients: A Minimally Invasive Method for the Detection of Bladder Cancer", *Clin. Cancer Res*., 8:35-40 (2002).
Valentine et al., "Detection of *Helicobacter pylori* by Using the Polymerase Chain Reaction", *J. Clin. Microbiol*., 29(4):689-695 (1991).
van Vollenhoven et al., "Polymerase chain reaction in the diagnosis of urinary tract tuberculosis", *Urol. Res*., 24:107-111 (1996).
Vonsover et al., "Detection of CMV in urine: comparison between DNA—DNA hybridization, virus isolation, and immunoelectron microscopy", *J. Virol. Methods*, 16:29-37 (1987).
Walker et al., "Multiplex strand displacement amplification (SDA) and detection of DNA sequences from *Mycobacterium tuberculosis* and other mycobacteria", *Nucl. Acids Res*., 22(13):2670-2677 (1994).
Wang et al., "Preferential Isolation of Fragmented DNA Enhances the Detection of Circulating Mutated k-*ras* DNA", *Clin. Chem*., 50(1):211-213 (2004).
Waters et al., "Partial sequence of the asexually expressed SU rRNA gene of *Plasmodium vivax", Nucl. Acids Res*., 17(5):2135 (1989).
Wegmuller et al., "Rapidly Progressive Glomerulonephritis Accompanying Legionnaires' Disease", *Arch Intern Med*., 145:1711-1713 (1985).
Welkos, S. L., "Plasmid-associated virulence factors of non-toxigenic ($pX01^-$) *Bacillus anthracis", Microbial Pathogenesis*, 10:183-198 (1991).
Zambardi et al., "Rapid diagnosis of *Mycobacterium tuberculosis* infections by an ELISA-like detection of polymerase chain reaction products", *Mol. Cell. Probes*, 9:91-99 (1995).

* cited by examiner

A

*B*
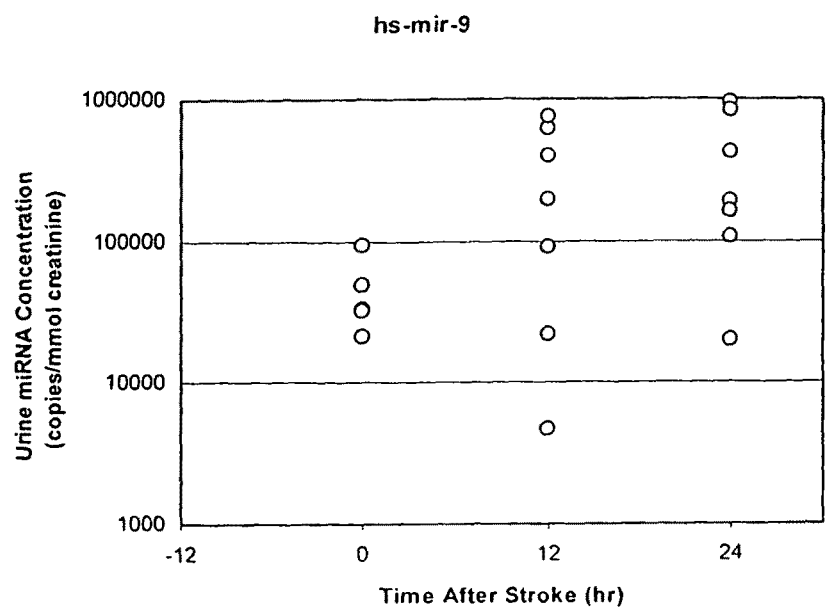
*C*
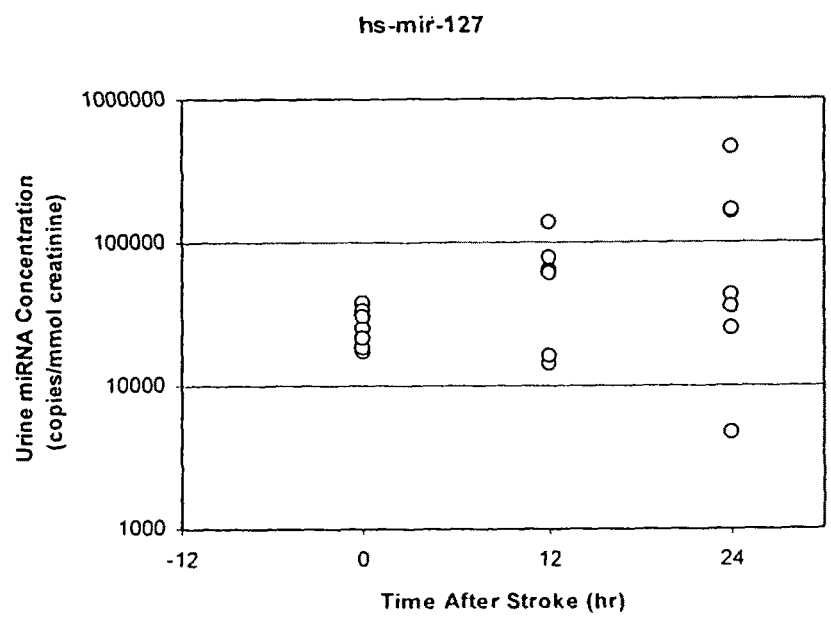

D
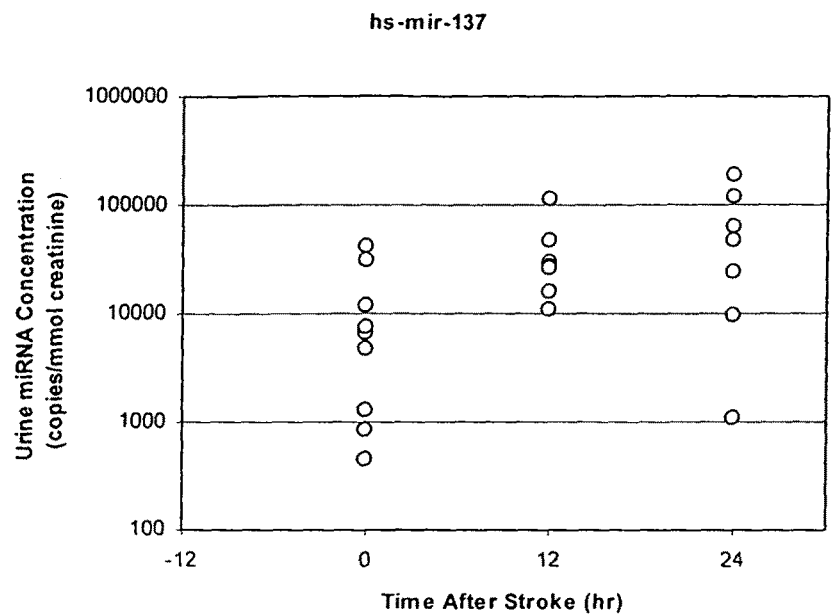
E
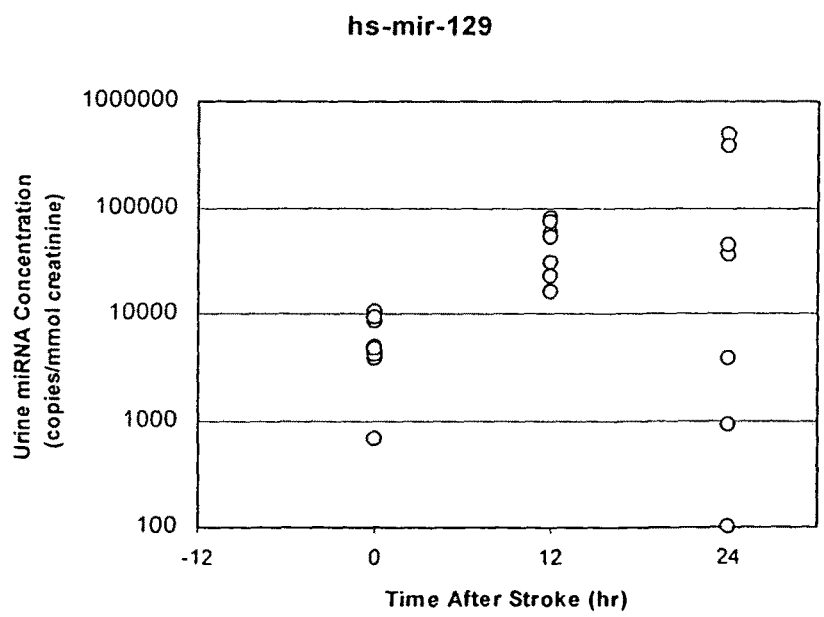

F
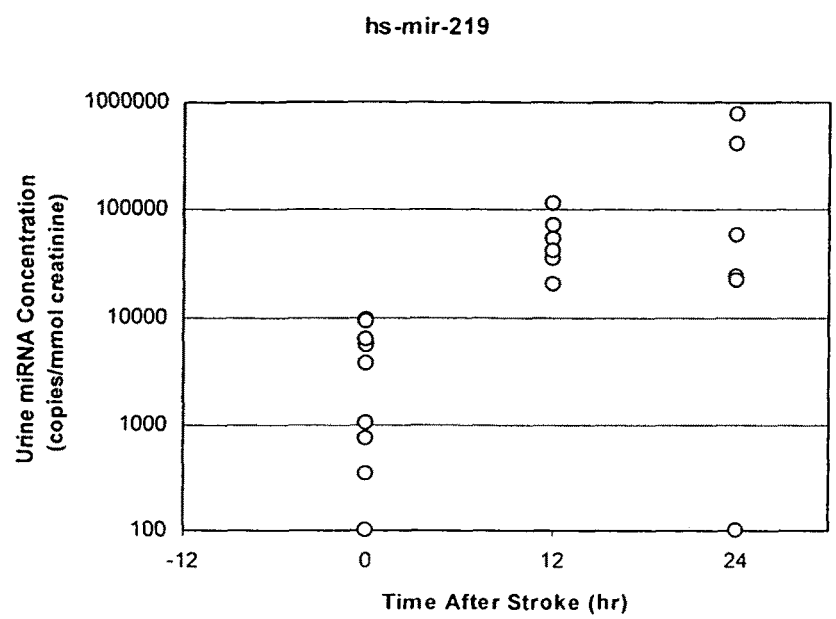
G
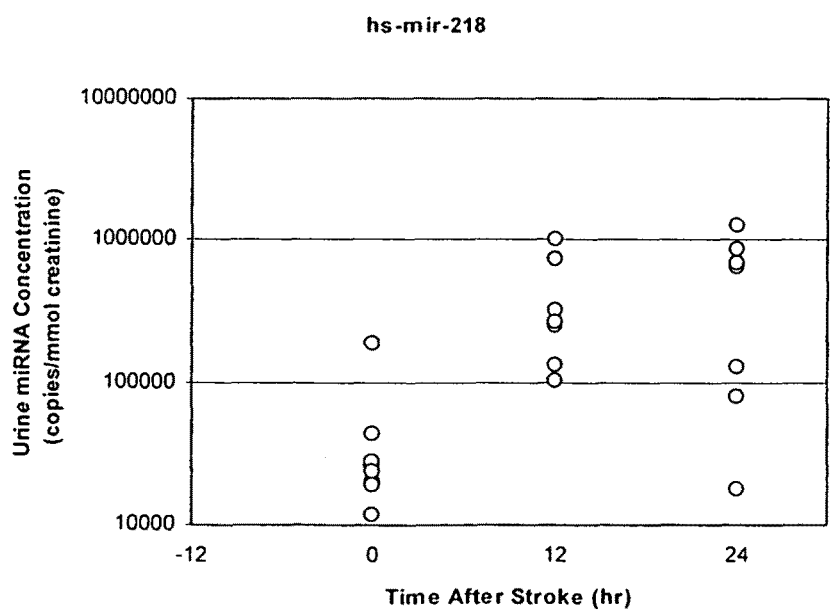

Figure 5
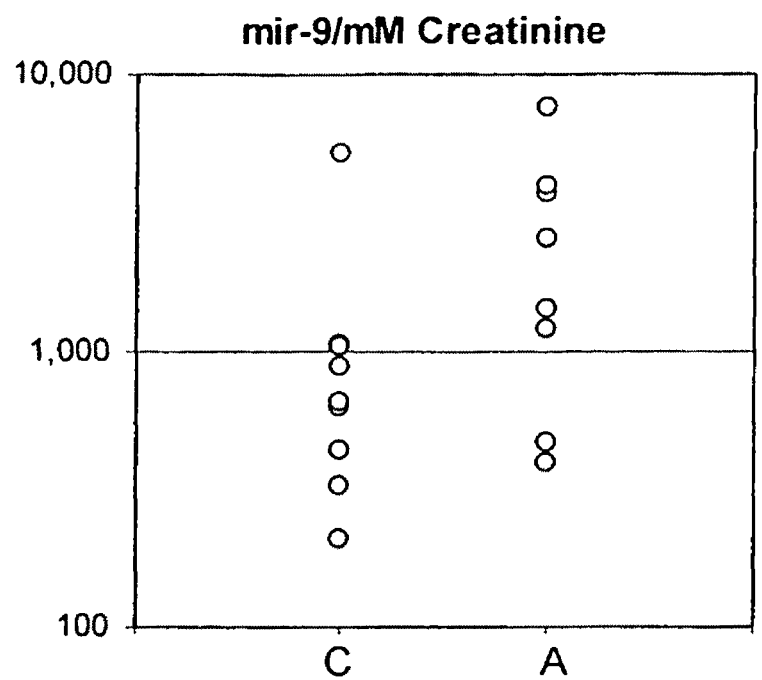
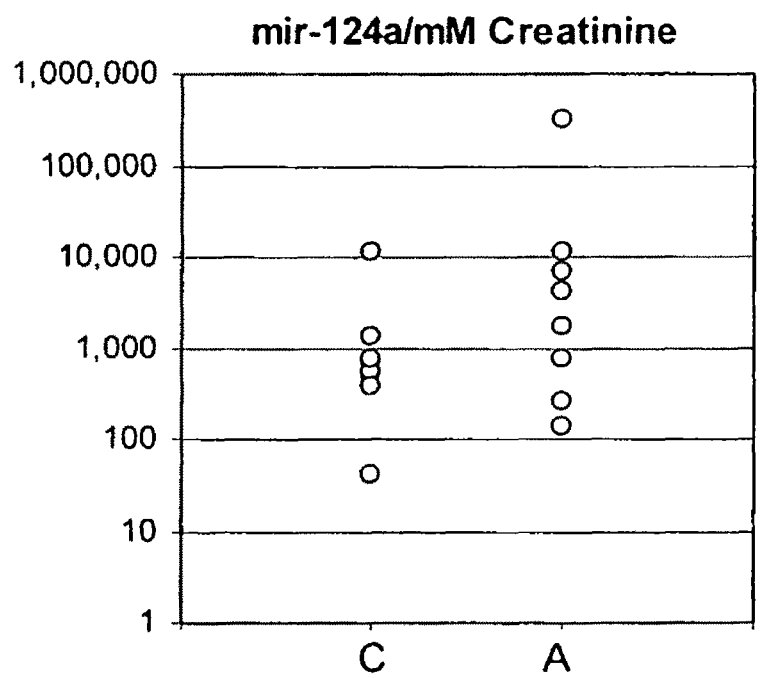

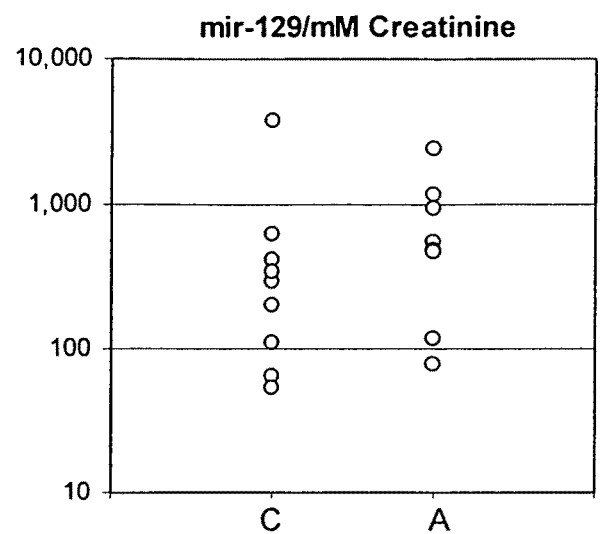
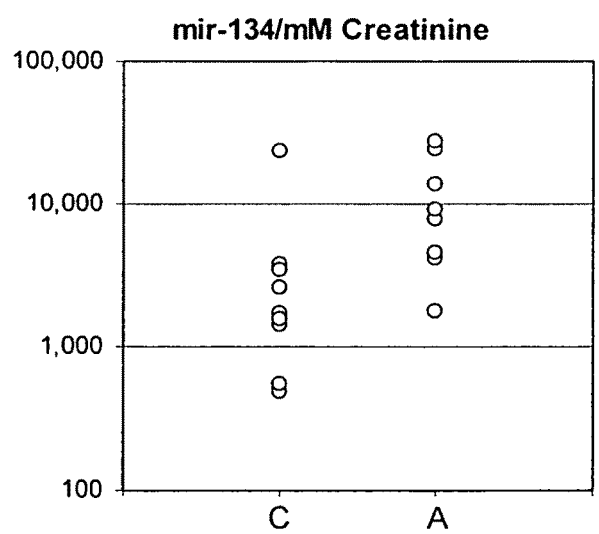

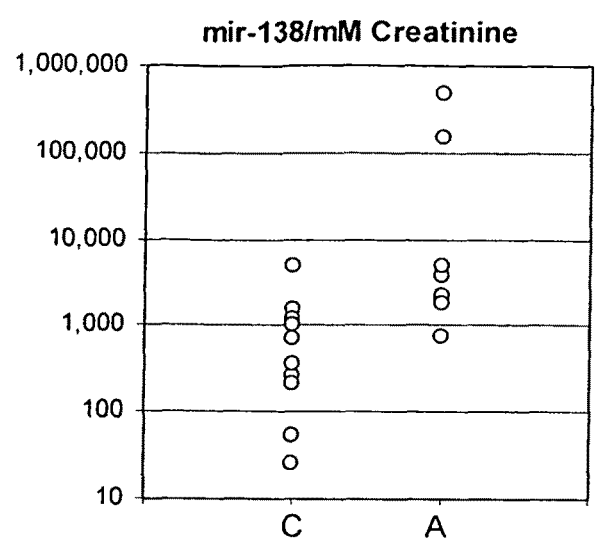

Figure 6
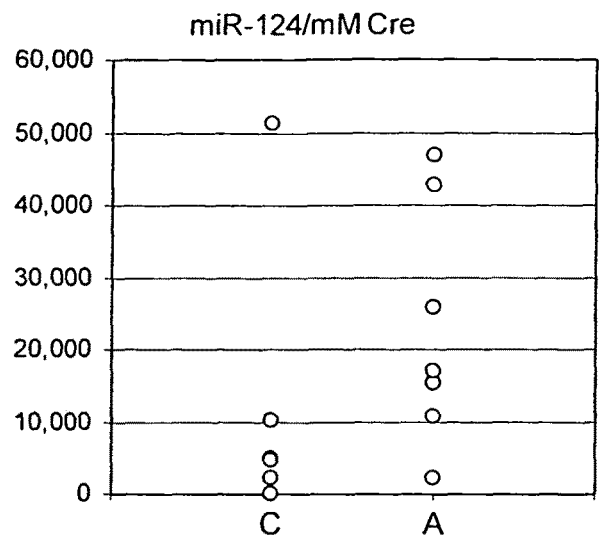
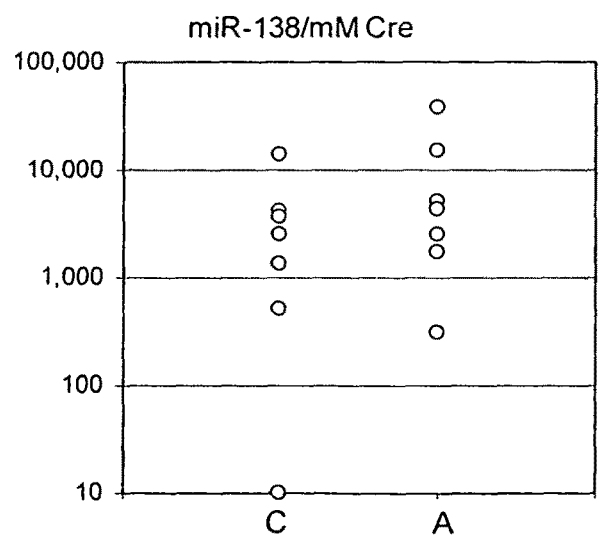

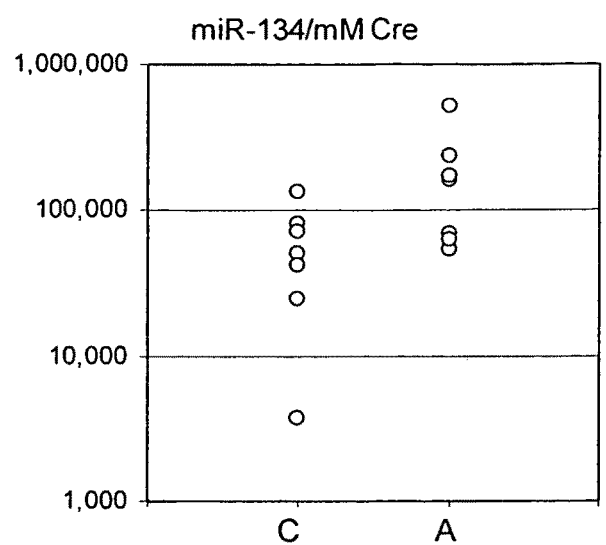

Figure 7
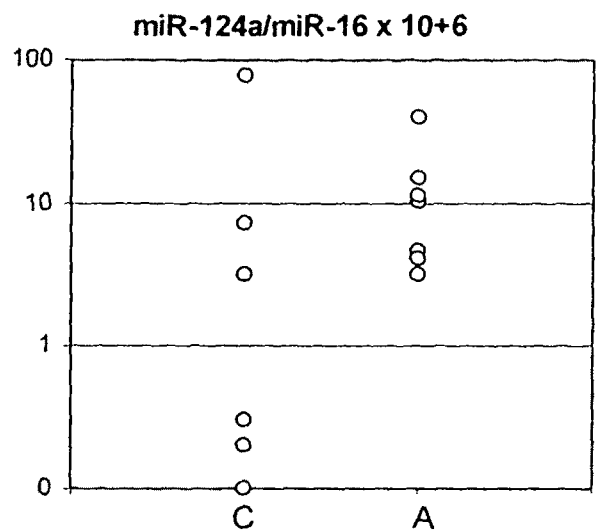
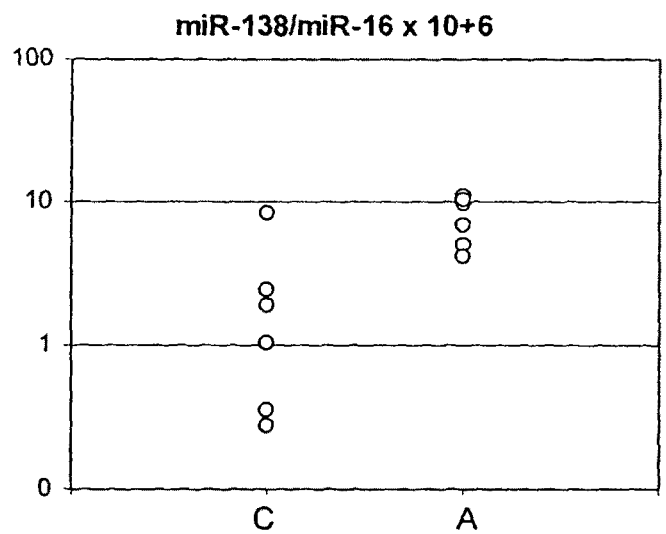

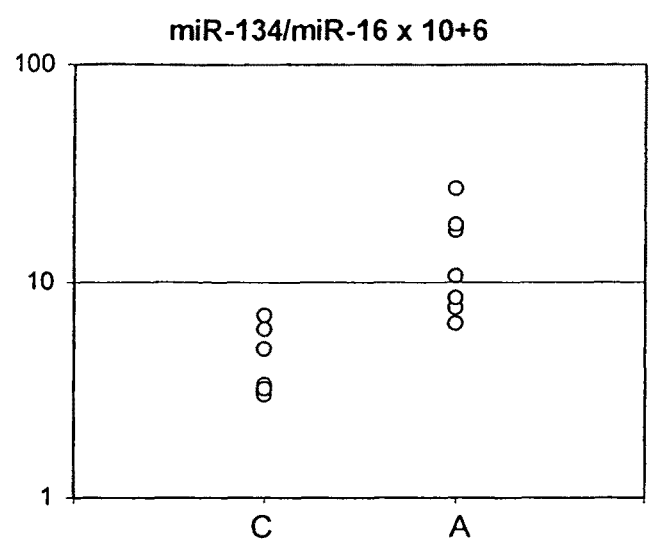

Figure 8
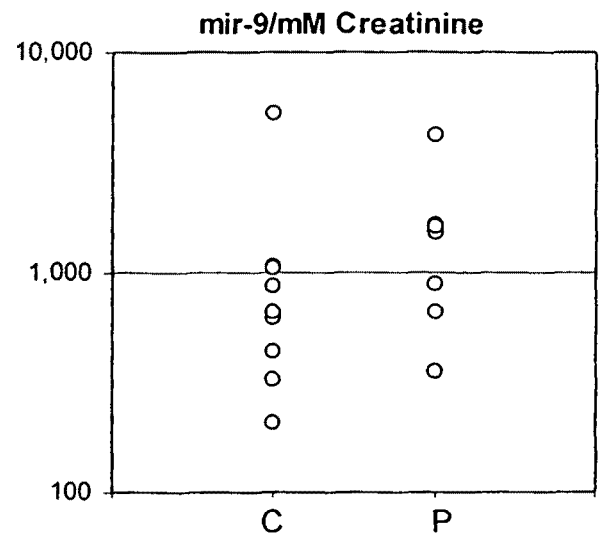
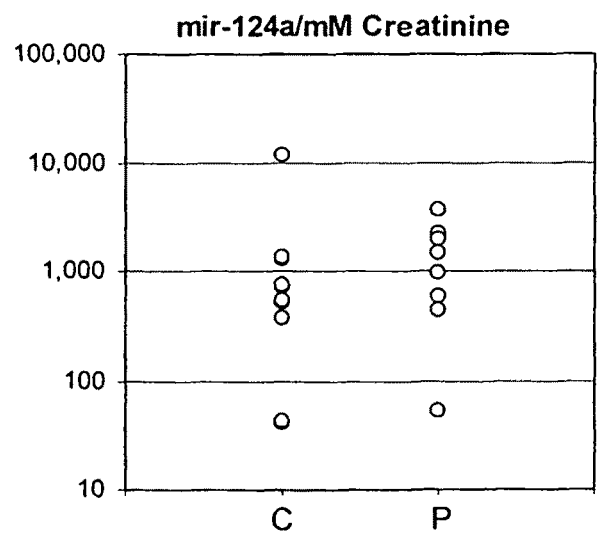

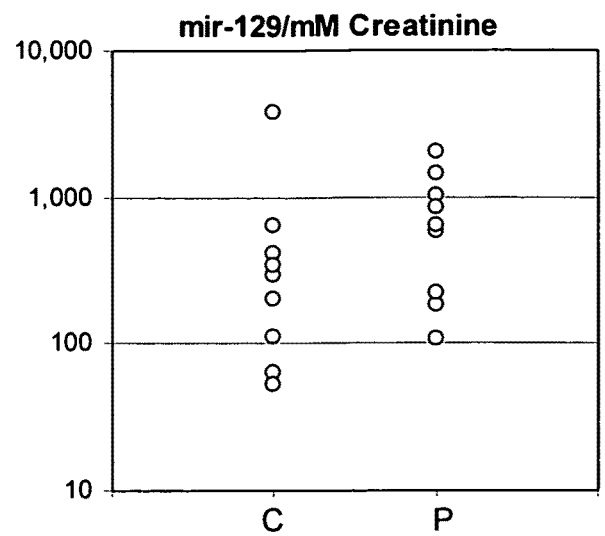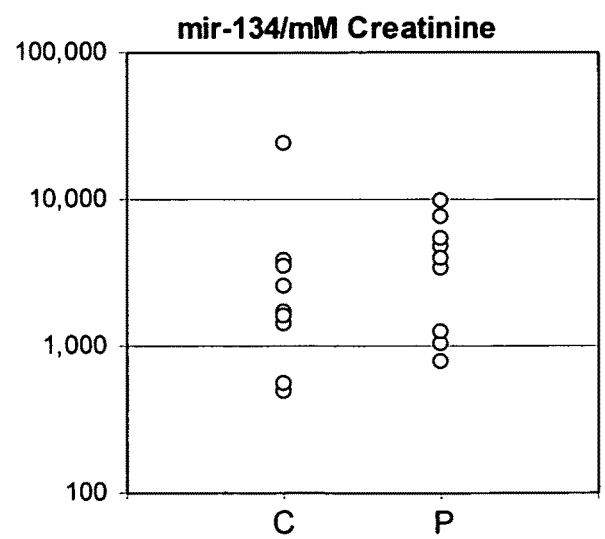

SEQUENCE LISTING

```
<160> NUMBER OF SEQ ID NOS: 27

<210> SEQ ID NO 1
<211> LENGTH: 22
<212> TYPE: RNA
<213> ORGANISM: Homo sapiens

<400> SEQUENCE: 1
ucggauccgu cugagcuugg cu                                              22

<210> SEQ ID NO 2
<211> LENGTH: 20
<212> TYPE: RNA
<213> ORGANISM: Homo sapiens

<400> SEQUENCE: 2
uugcauaguc acaaaaguga                                                 20

<210> SEQ ID NO 3
<211> LENGTH: 21
<212> TYPE: RNA
<213> ORGANISM: Homo sapiens

<400> SEQUENCE: 3
cuuuuugcgg ucugggcuug c                                               21

<210> SEQ ID NO 4
<211> LENGTH: 22
<212> TYPE: RNA
<213> ORGANISM: Homo sapiens

<400> SEQUENCE: 4
uauugcuuaa gaauacgcgu ag                                              22
```

```
<210> SEQ ID NO 5
<211> LENGTH: 21
<212> TYPE: RNA
<213> ORGANISM: Homo sapiens

<400> SEQUENCE: 5
uugugcuuga ucuaaccaug u                                          21

<210> SEQ ID NO 6
<211> LENGTH: 21
<212> TYPE: RNA
<213> ORGANISM: Homo sapiens

<400> SEQUENCE: 6
ugauugucca aacgcaauuc u                                          21

<210> SEQ ID NO 7
<211> LENGTH: 22
<212> TYPE: RNA
<213> ORGANISM: Homo sapiens

<400> SEQUENCE: 7
ucacagugaa ccggucucuu uu                                         22

<210> SEQ ID NO 8
<211> LENGTH: 23
<212> TYPE: RNA
<213> ORGANISM: Homo sapiens

<400> SEQUENCE: 8
ucuuugguua ucuagcugua uga                                        23

<210> SEQ ID NO 9
<211> LENGTH: 17
<212> TYPE: RNA
<213> ORGANISM: Homo sapiens

<400> SEQUENCE: 9
agcugguguu gugaauc                                               17

<210> SEQ ID NO 10
<211> LENGTH: 21
<212> TYPE: RNA
<213> ORGANISM: Homo sapiens

<400> SEQUENCE: 10
ugugacuggu ugaccagagg g                                          21

<210> SEQ ID NO 11
<211> LENGTH: 22
<212> TYPE: RNA
<213> ORGANISM: Homo sapiens

<400> SEQUENCE: 11
uuaaggcacg cggugaaugc ca                                         22

<210> SEQ ID NO 12
<211> LENGTH: 23
<212> TYPE: RNA
<213> ORGANISM: Homo sapiens

<400> SEQUENCE: 12
uggaguguga caauggguguu ugu                                       23
```

```
<210> SEQ ID NO 13
<211> LENGTH: 22
<212> TYPE: RNA
<213> ORGANISM: Homo sapiens

<400> SEQUENCE: 13
uugguccccu ucaaccagcu gu                                              22

<210> SEQ ID NO 14
<211> LENGTH: 21
<212> TYPE: RNA
<213> ORGANISM: Homo sapiens

<400> SEQUENCE: 14
uggaauguaa agaaguaugu a                                               21

<210> SEQ ID NO 15
<211> LENGTH: 23
<212> TYPE: RNA
<213> ORGANISM: Homo sapiens

<400> SEQUENCE: 15
ucaagagcaa uaacgaaaaa ugu                                             23

<210> SEQ ID NO 16
<211> LENGTH: 22
<212> TYPE: RNA
<213> ORGANISM: Homo sapiens

<400> SEQUENCE: 16
uagcagcacg uaaauauugg cg                                              22

<210> SEQ ID NO 17
<211> LENGTH: 21
<212> TYPE: RNA
<213> ORGANISM: Homo sapiens

<400> SEQUENCE: 17
augaccuaug aauugacaga c                                               21

<210> SEQ ID NO 18
<211> LENGTH: 22
<212> TYPE: RNA
<213> ORGANISM: Homo sapiens

<400> SEQUENCE: 18
uauggcuuuu cauuccuaug ug                                              22

<210> SEQ ID NO 19
<211> LENGTH: 22
<212> TYPE: RNA
<213> ORGANISM: Homo sapiens

<400> SEQUENCE: 19
aucgugcauc cuuuuagagu gu                                              22

<210> SEQ ID NO 20
<211> LENGTH: 22
<212> TYPE: RNA
<213> ORGANISM: Homo sapiens

<400> SEQUENCE: 20
aaagcgcuuc ccuucagagu gu                                              22
```

<210> SEQ ID NO 21
<211> LENGTH: 22
<212> TYPE: RNA
<213> ORGANISM: Homo sapiens

<400> SEQUENCE: 21
cgcaccacua gucaccaggu gu                                            22

<210> SEQ ID NO 22
<211> LENGTH: 23
<212> TYPE: RNA
<213> ORGANISM: Homo sapiens

<400> SEQUENCE: 22
uagcaccgcu auccacuaug ucu                                           23

<210> SEQ ID NO 23
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtcgtatcca gtgcagggtc cgaggtattc gcactggata cgacacacct              50

<210> SEQ ID NO 24
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtcgtatcca gtgcagggtc cgaggtattc gcactggata cgacagacat              50

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cgccgcacca ctagtcac                                                 18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cgctagcacc gctatcca                                                 18

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Synthetic -continued

```
   primer

<400> SEQUENCE: 27
gtgcagggtc cgaggt                                                     16
```

METHODS OF DETECTING CELL-FREE MIRNA IN URINE AND BLOOD

RELATED APPLICATIONS

This application claims the benefit of U.S. Provisional Application No. 60/965,871, filed on Aug. 22, 2007, the contents of which are incorporated herein by reference in its entirety.

FIELD OF THE INVENTION

The invention provides non-invasive methods for isolation and detection of cell-free small RNA, in particular microRNA (miRNA) sequences in bodily fluid. More specifically, the present invention encompasses methods of detecting in vivo cell death by analyzing urine and other body fluids for miRNA levels for clinical diagnosis and treatment monitoring.

BACKGROUND OF THE INVENTION

Cell death is a normal component of development and functioning of multicellular organisms. Being a natural process, cell death is involved in the pathology of numerous diseases caused by internal factors. Cell death also accompanies diseases caused by external physical, chemical, of biological agents.

There exist two major types of cell death, necrosis and apoptosis, marked by different morphological and molecular characteristics (Kerr et al., Br. J. Cancer. 26, 239-257 (1972); Umansky, Theor. Biol. 97, 591-602 (1982); Umansky et al., Adv Pharmacol. 41, 383-407 (1997); Ameisen, Cell Death Differ. 11, 4-10 (2004); Lockshin et al. Int J Biochem Cell Biol. 36, 2405-19 (2004); G. Kroemer, et al., Cell Death and Differentiation 12, 1463-1467 (2005)). Necrosis is considered to be catastrophic metabolic failure resulting directly from severe molecular and/or structural damage and leads to inflammation and secondary damage to surrounding cells. Apoptosis is a much more prevalent biological phenomenon than necrosis and can be induced by specific signals such as hormones, cytokines, by absence of specific signal such as growth or adhesion factors, or by molecular damage that does not cause catastrophic loss of integrity. Apoptosis is a result of an active cellular response involving initiation of an orderly and specific cascade of molecular events. Apoptosis leads to the appearance of distinctive chromatin condensation and margination, nuclear fragmentation, cell shrinkage, membrane blebbing and enzymatic internucleosomal fragmentation of nuclear DNA (Umansky et al., Biochim Biophys Acta. 655, 9-17 (1981); Arends et al., Am J. Pathol. 136, 593-608 (1990)). Other more rare forms of cell death, characterized by specific morphology, for example, so called autophagic cell death have also been described (Bredesen et al., Stroke. 38(2 Suppl):652-660 (2007).

Independent of a specific mechanism and type of cell death, methods to detect dying cell types are important for diagnosis of various diseases, critical for disease and treatment monitoring, and helpful for differential diagnosis. Besides, the methods capable of detection of specific cell death in vivo are useful for developing drugs aiming at prevention or induction of cell death as well as for analysis of the cytotoxicity of the newly developed drugs.

There are some clinical tests for diagnosis of disease-related excessive cell death based on detection of tissue specific markers, such as for example antigens, enzymes and other proteins in blood or in other bodily fluids. Measurement of the activity of liver-specific enzymes in blood, for example, is a widely used method for evaluation of hepatocyte death (Amacher, et al., Regul Toxicol Pharmacol. April; 27(2):119-130 (1988); Salaspuro, et al., Enzyme. 37:87-107 (1987); Herlong, Hosp. Pract. (Off Ed).29(11):32-38 (1994)). Evaluation of the level of cardiomyocyte specific antigens has also been used for diagnosis of the myocardial infarction (Mair et al., Clin Chem Lab Med. 37:1077-1084 (1999); Nunes et al., Rev Port Cardiol. 20:785-788 (2001)). However, the number of such techniques is limited to diseases in which a marker and a method of detection are known in order for the analysis to provide meaningful, tissue-specific results (Oh S et al., Curr Gastroenterol Rep. 3:12-18 (2001); Rochling et al., Clin Cornerstone. 3(6):1-12 (2001)). Other methods require invasive biopsy of specific tissues suspected of having a diseased condition to get a specimen for analysis. However, biopsy of some organs and tissues, for example brain is highly invasive and often difficult to perform.

It is well known that apoptosis, or programmed cell death, which is a major form of cell death in the mammalian organism, is accompanied by internucleosomal fragmentation of nuclear DNA. Many laboratories have demonstrated that a portion of this DNA appears in blood (Lo Y. M. Ann NY Acad Sci. 945:1-7 (2001); Lichtenstein et al., Ann N Y Acad Sci. 945:239-249 (2001); Taback et al., Curr Opin Mol Ther. 6:273-278 (2004); Bischoff et al., Hum Reprod Update. 8:493-500, (2002)). It has also been shown that this fragmented DNA, called transrenal DNA (Tr-DNA) crosses the kidney barrier and can be detected in the urine (Botezatu et al., Clin Chem. 46:1078-1084, (2000); Su et al., J Mol Diagn. 6:101-107 (2004); Su et al., Ann N Y Acad Sci. 1022:81-89 (2004).

Although both cell-free plasma DNA and Tr-DNA may be used as diagnostic tools, they provide a rather limited approach when evaluating tissue specific events, such as cell death. Thus analytical methods that are non-invasive, and provide a broader range of indications of specific pathology, due to their ability to detect levels of dying cells in particular tissues and organs, would be useful for diagnosing and monitoring the state of various diseases or pathological conditions in patients. In addition, tissue specific analytical methods that provide the means for monitoring the response of a patient to a disease therapy would be useful to determine the therapy effectiveness, and in the case of drug treatment, the optimum dosage required for drug administration.

To address these problems, the instant invention is focused on the use of micro RNA (miRNA) as a diagnostic tool to monitor in vivo cell death in bodily fluids, such as for example serum and urine. Unlike cell-free plasma DNA and Tr-DNA, many miRNAs exhibit cell, tissue and organ specific expression profiles (Liang et al., Genomics, 8:166 (2007); Lukiw et al, Neuroreport. 18:297-300 (2007); Lagos-Quintana et al., Curr Biol. 12:735-739 (2002); Chen et al., Nat Genet. 38:228-233 (2006); Beuvink et al., J. Nucleic Acids Res. 35:e52 (2007)). Furthermore, correlation of miRNA cell and tissue specific profiles with different pathologies and tumor types have been demonstrated (Visone R., et al. Oncogene. 26:7590-7595 (2007); Nelson et al., Neuropathol Exp Neurol. 66:461-468 (2007); Negrini et al., J Cell Sci. 120:1833-1840 (2007); Chang et al., Annu Rev Genomics Hum Genet. 8:215-239 (2007); Jay et al., Cell Biol. 26:293-300 (2007)).

Thus, the instant invention provides methods for measuring in vivo cell death by detection of tissue-specific miRNAs, characteristic of a specific pathology, in body fluids, such as for example serum and urine. The instant methods based on detection of miRNAs in bodily fluids are used for further development of diagnostic or monitoring tests.

SUMMARY OF THE INVENTION

The instant invention relates to a novel method for detecting and measuring in vivo cell-death by analyzing levels of specific miRNA sequences in cell-free nucleic acids obtained from bodily fluids, said miRNA originating from cells dying throughout the body, and using the obtained analytical result to determine state of a disease or abnormal medical condition in a patient.

The methods of the instant invention are based on adsorption of cell-free nucleic acids on and elution from anion-exchangers, which makes it possible to concentrate and isolate nucleic acid fragments larger then 10 nucleotides. Specifically, the instant invention demonstrates: (i) the presence of miRNA in body fluids; (ii) detection in urine of miRNA that originated from organs located outside of urinary system, which means that they have crossed the kidney barrier, such as for example, transrenal miRNA (Tr-miRNA); iii) detection of miRNA in serum (iv) pathology associated with cell death in a particular cell, tissue and/or organ is accompanied by changes in levels of miRNA specific for the said organ.

The present invention provides a method of detecting and quantitating cell, tissue and/or organ-specific cell-free miRNAs in body fluid for evaluation of in vivo cell death in various tissue and organs, wherein in vivo cell death is associated with a disorder of a particular tissue and/or organ comprising obtaining a body fluid sample from a subject; and analyzing said body fluid sample for one or more specific sequences of miRNA, wherein said analyzing comprises the step of detecting said miRNA with a primer and/or probe that is substantially complementary to a part of said specific miRNA sequences. In some embodiments of the present invention, excessive or insufficient in vivo cell death is associated with a disorder of particular tissue.

In one embodiment of the present invention, the body fluid is urine. In another embodiment, the present method of analysis of a urine sample includes a technique selected from the group consisting of hybridization, cycling probe reaction, polymerase chain reaction, nested polymerase chain reaction, PCR to analyze single strand conformation polymorphisms and ligase chain reaction. In yet another embodiment, nucleic acid degradation in said urine sample is reduced.

The method of the present invention includes reducing nucleic acid degradation comprising inhibiting nuclease activity by addition of RNAse inhibitor(s), heat inactivation, or by treating said urine sample with a compound selected from the group consisting of: guanidine-HCl, guanidine isothiocyanate, N-lauroylsarcosine, and sodium dodecylsulphate. In one embodiment of the present invention, urine sample has been held in the bladder less than 12 hours.

In one embodiment of the present invention, the body fluid is serum. The method of the present invention includes analysis of a serum sample including a technique selected from the group consisting of hybridization, cycling probe reaction, polymerase chain reaction, nested polymerase chain reaction, PCR to analyze single strand conformation polymorphisms and ligase chain reaction.

In yet another embodiment, the method of the instant invention involves detecting cell-free miRNAs, as a specific marker for the specific disorder associated with excessive or insufficient cell death in a tissue or organ. Optionally, said disorder is a pathogen infection. Preferably, said pathogen is a virus. More preferably, said virus is an Epstein-Barr virus. Optionally, said disorder is a brain stroke, Alzheimer's disease, Parkinson's disease, associated with pregnancy and/or fetus or Down syndrome.

The present invention provides a method of detecting in urine cell-free miRNAs, originating in different organs and tissues, including areas other than urinary system, in a subject as a result of disorder associated with excessive or insufficient cell death in a tissue or organ, comprising obtaining a urine sample from a subject; and analyzing said urine sample for one or more specific sequences of miRNA wherein said analyzing comprises the step of detecting said miRNA with a primer and/or probe that is substantially complementary to a part of said specific miRNA sequences.

The method of the present invention provides a method of disease and/or treatment monitoring in a subject by quantitative analysis of specific cell-free miRNAs in a body fluid, comprising periodically obtaining a body fluid sample from a subject; and analyzing said sample for one or more specific sequences of miRNA that are specific/over-expressed in cells, tissue or organ of interest, wherein said analyzing comprises the step of detecting said miRNA with primers and/or probe that is substantially complementary to a part of said specific miRNA sequences. In one embodiment, the body fluid is urine. In another embodiment, the body fluid is serum.

BRIEF DESCRIPTION OF THE DRAWINGS

The foregoing and other objects, features, and advantages of the invention will be apparent from the more particular description of embodiments of the invention, as illustrated in the accompanying drawings. The drawings are not necessary to scale, emphasis instead being placed upon illustrating the principles of the invention.

FIG. 5 is a dot plot representation of the normalized concentrations of miRNA in unfiltered urine samples of patients with Alzheimer's disease and age matched controls.

FIG. 6 is a dot plot representation of the normalized concentrations of miRNA in filtered urine samples of patients with Alzheimer's disease and age matched controls.

FIG. 7 is a dot plot representation of the normalized concentrations of miRNA in serum samples of patients with Alzheimer's disease and age matched controls.

FIG. 8 is a dot plot representation of the normalized concentrations of miRNA in urine samples of patients with Parkinson's disease and age matched controls.

DETAILED DESCRIPTION OF THE INVENTION

Figure 1:
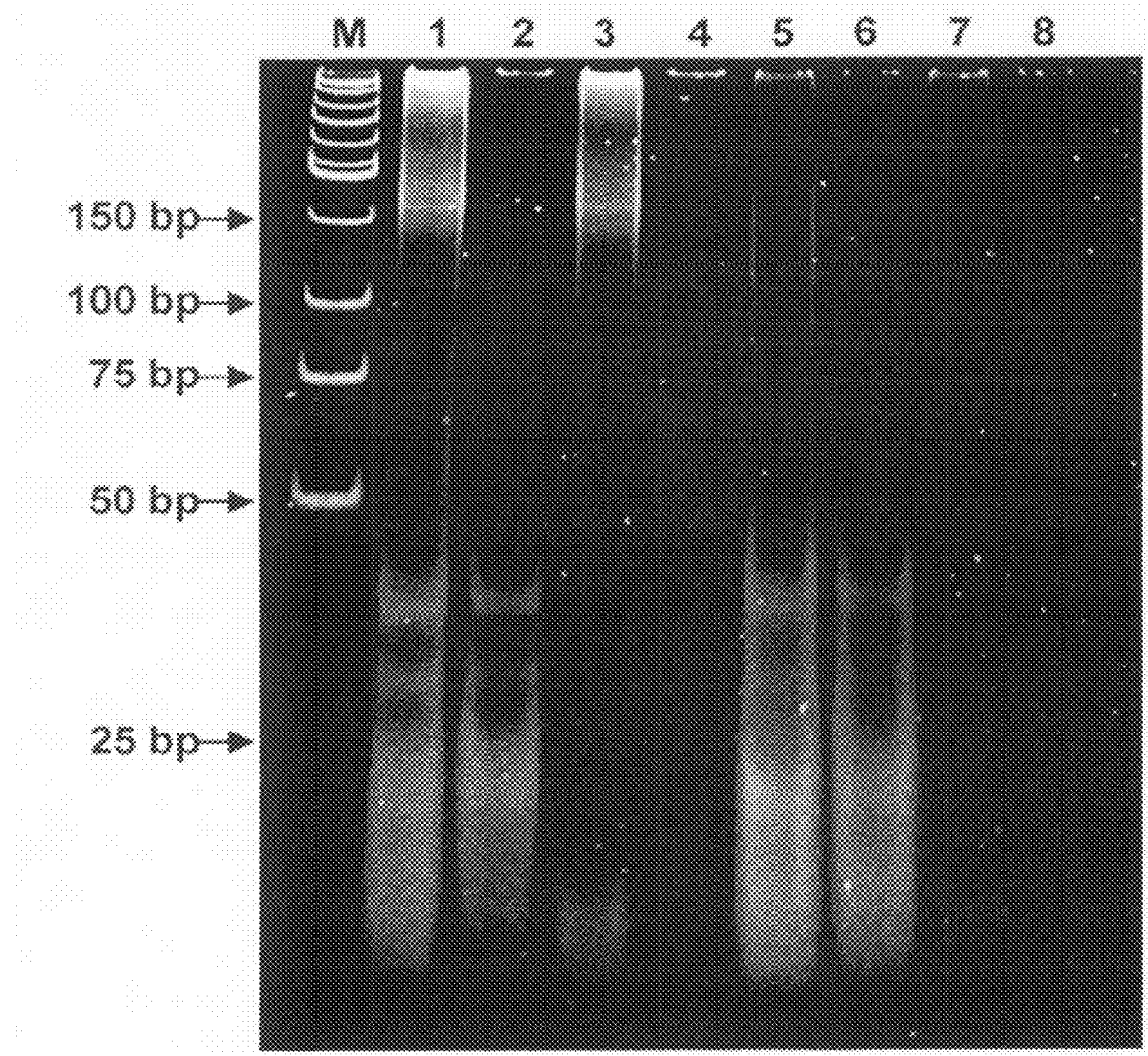
FIG. 1 is a photograph of a polyacrylamide gel electrophoresis of nucleic acids extracted from filtered urine using Q-Sepharose™.

The technology of this invention is based on the discovery that small RNAs, in particular specific micro RNAs (miRNAs), including transrenal miRNA (Tr-miRNA), are presented in bodily fluids and their concentrations reflect cell death associated with organ damage or other pathology. The presence of these nucleic acid sequences at levels lower or higher than that of a control group is therefore an indication that an abnormality or pathological condition is likely present in the patient from whom the sample was obtained.

The methods of the present invention offer improvements over previous methods of diagnosis, detection and monitoring due to their inherently non-invasive nature.

To facilitate the understanding of the invention, a number of terms are defined below:

The term "primer" refers to an oligonucleotide which is capable of acting as a point of initiation of synthesis when placed under conditions in which primer extension is initiated. An oligonucleotide "primer" can occur naturally, as in a purified restriction digest or be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

A "target" nucleic acid is a miRNA sequence to be evaluated by hybridization, amplification or any other means of analyzing a nucleic acid sequence, including a combination of analysis methods.

"Hybridization" methods involve the annealing of a complementary sequence to the target nucleic acid (the sequence to be analyzed). The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology. Hybridization encompasses, but not be limited to, slot, dot and blot hybridization techniques.

It is important for some diagnostic applications to determine whether the hybridization represents complete or partial complementarity. For example, where it is desired to detect simply the presence or absence of pathogen miRNA, it is only important that the hybridization method ensures hybridization when the relevant sequence is present; conditions can be selected where both partially complementary probes and completely complementary probes will hybridize. Other diagnostic applications, however, may require that the hybridization method distinguish between partial and complete complementarity. It may be of interest to detect genetic polymorphisms.

The term "probe" as used herein refers to an oligonucleotide (i.e., a sequence of nucleotides), whether occurring naturally as in a purified restriction digest or produced synthetically, which forms a duplex structure or other complex with a sequence of another nucleic acid, due to complementarity or other means of reproducible attractive interaction, of at least one sequence in the probe with a sequence in the other nucleic acid. Probes are useful in the detection, identification and isolation of particular gene sequences. It is contemplated that any probe used in the present invention will be labeled with any "reporter molecule," so that it is detectable in any detection system, including, but not limited to, enzyme (e.g., ELISA, as well as enzyme—based histochemical assays), fluorescent, radioactive, and luminescent systems. It is further contemplated that the oligonucleotide of interest (i.e., to be detected) will be labeled with a reporter molecule. It is also contemplated that both the probe and oligonucleotide of interest will be labeled. It is not intended that the present invention be limited to any particular detection system or label.

As used herein, the term "miRNA" is a subclass of small non-coding single stranded RNA, approximately 18-23 nucleotides in length which plays an important role in regulation of metabolic processes, particularly due to their involvement in regulation of stability and translation of mRNA encoding specific proteins. miRNA also participate in other important processes, like heterochromatin formation and genome rearrangement.

The terms "excessive" and "insufficient" in vivo cell death describe the situation when the number of cells dying in a particular organ or tissue is respectively higher or lower than in age and gender matched controls.

As used herein, the terms "purified", "decontaminated" and "sterilized" refer to the removal of contaminant(s) from a sample.

As used herein, the terms "substantially purified" and "substantially isolated" refer to nucleic acid sequences that are removed from their natural environment, isolated or separated, and are preferably 60% free, more preferably 75% free, and most preferably 90% free from other components with which they are naturally associated. An "isolated polynucleotide" is therefore a substantially purified polynucleotide. It is contemplated that to practice the methods of the present invention polynucleotides can be, but need not be substantially purified. A variety of methods for the detection of nucleic acid sequences in unpurified form are known in the art.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

The term "urinary tract" as used herein refers to the organs and ducts which participate in the secretion and elimination of urine from the body.

"Patient" or "subject" as the terms are used herein, refer to the recipient of the treatment. Mammalian and non-mammalian patients are included. In a specific embodiment, the patient is a mammal, such as a human, canine, murine, feline, bovine, ovine, swine, or caprine. In a particular embodiment, the patient is a human.

In one embodiment of the present invention, the detected miRNAs originate from and are specifically expressed in a specific cell type, tissue, or organ in the body, wherein alterations in the level of said miRNAs are indicative of acute pathology of said tissue, such as for example acute myocardial infarction associated with death of cardiomyocytes; brain stroke associated with death of neurons and glial cells; hepatitis or liver cirrhosis associated with hepatocyte death caused by a viral or other infection or by action of toxic agents; acute pancreatitis associated with death of different pancreatic cells; rejection of a transplanted organ associated with excessive cell death in the transplanted organ; traumatic damage of various organs; numerous acute infections, for example tuberculosis associated with cell death in lungs and/or other infected organs.

In another embodiment of the present invention, the detected miRNAs originate from and are specifically expressed in a specific cell type, tissue, or organ in the body, wherein alterations in the level of said miRNAs are indicative of chronic pathology of said tissue, such as for example Alzheimer's disease, Parkinson disease, frontotemporal dementia and other diseases of the central nervous system that are caused or accompanied by neuronal death; chronic heart failure associated with the death of cardiomyocytes, emphysema associated with death of lung cells; diabetes type 1 associated with the death of pancreatic beta cells, glomerulonephritis associated with the death of kidney cells, precancerous conditions associated with the apoptotic death of actively proliferating precancerous cells, cancers associated with massive necrotic cell death due to insufficient blood supply, and cell death in chronically infected organs or tissues.

In yet another embodiment of the present invention, the detected miRNAs originate from and are specifically expressed in a specific cell type, tissue, or organ in the body, and alterations in the level of said miRNAs are indicative of cytotoxic effects of physical and chemical agents, such as for example radiation associated with relatively low doses that kill bone marrow cells higher doses that lead to the death of epithelial cells of gastrointestinal system, and even higher doses that kill brain neurons; and chemical cytotoxicity, associated with cell death in different organ and tissues induced by natural or synthetic toxic compounds.

In yet another embodiment of the present invention, the detected miRNAs originate from and are specifically expressed in a specific cell type, tissue, or organ in the body and can be used for prognosis of disease outcome. Changes in the levels of respective miRNAs, that are indicative of disease progression/regression, success of therapeutic or surgical intervention, are used for disease and treatment monitoring.

In another embodiment of the invention, the detected miRNAs originate from transplanted cells, tissues, or organs and their levels are indicative of rejection episodes and corresponding treatment.

In another embodiment of the invention, the detected miRNAs originate from a pathogen and are used for infection diagnosis and monitoring. In a specific embodiment of the instant invention, the pathogen is a virus, for example Epstein-Barr virus.

In yet another embodiment of the invention, the detected miRNAs originate from cells of an infected organ and can be used for diagnosis support, evaluation of infected tissue damage, and further disease and treatment monitoring.

In yet another embodiment of the invention, the detected miRNAs originate from the fetus of a pregnant female, and are characteristic of a condition or pathology of the fetus, such as for example pre-eclampsia, which is characterized by excessive death of trophoblasts in placenta. In yet another embodiment, the detected miRNAs originate from a fetus of a pregnant female, and are characteristic of a condition or pathology of the fetus, such as for example Down syndrome and other trisomies accompanied by the delay of organ development and excessive or inhibited cell death.

In yet another embodiment of the invention, the information about the levels of tissue or cell-specific miRNAs alone or in combination with other markers are used for diagnosis or monitoring of cancer and pre-cancerous conditions, such as for example liver cancer, kidney cancer, prostate cancer, colorectal cancer, pancreatic cancer and other known cancers.

In some embodiments, the levels of cell- and/or tissue-specific miRNAs are normalized using the levels of ubiquitous miRNA in serum, the levels of albumin or creatinine in urine, or the levels of placenta-specific miRNAs for normalization of other tissue-specific fetal miRNAs.

In one aspect of the invention, the step of analyzing said urine sample to detect specific miRNAs includes a technique selected from the group consisting of hybridization, cycling probe reaction, polymerase chain reaction, nested polymerase chain reaction, PCR to analyze single strand conformation polymorphisms and ligase chain reaction.

In certain aspects of the invention, the nucleic acid degradation in said urine sample is reduced. The method of reducing nucleic acid degradation comprises inhibiting nuclease activity by use of RNAse inhibitors, or by treating said urine sample with a compound selected from the group consisting of: guanidine-HCl, guanidine isothiocyanate, N-lauroylsarcosine, and sodium dodecylsulphate. In another aspect of the invention, said urine sample has been held in the bladder less than 12 hours.

In one embodiment of the present invention, the miRNA sequences measured are specifically related to tissues in the body, which may be selected from but are not limited to, lung, heart, liver, nervous system, brain, blood, kidney, bone, eye or pancreas.

The tissues selected for the analysis may be normal or abnormal (e.g., malignant). Malignant tissues and tumors include carcinomas, sarcomas, melanomas and leukemia generally and more specifically selected from malignant tissues and tumors associated with biliary tract cancer, bladder cell carcinoma, bone cancer, brain and CNS cancer, breast cancer, cervical cancer, choriocarcinoma, chronic myelogenous leukemia, colon cancer, connective tissue cancer, cutaneous T-cell leukemia, endometrial cancer, esophageal cancer, eye cancer, follicular lymphoma, gastric cancer, hairy cell leukemia, Hodgkin's lymphoma, intraepithelial neoplasms, larynx cancer, lymphomas, liver cancer, lung cancer (e.g. small cell and non-small cell), melanoma, multiple myeloma, neuroblastomas, oral cavity cancer, ovarian cancer, pancreatic cancer, prostate cancer, rectal cancer, renal cell carcinoma, sarcomas, skin cancer, squamous cell carcinoma, testicular cancer, thyroid cancer, and renal cancer. The method may be used to distinguish between benign and malignant tumors.

Subjects from whom such tissue samples may be harvested include those at risk of developing a cancer. A subject at risk of developing a cancer is one who has a high probability of developing cancer (e.g., a probability that is greater than the probability within the general public). These subjects include, for instance, subjects having a genetic abnormality, the presence of which has been demonstrated to have a correlative relation to a likelihood of developing a cancer that is greater than the likelihood for the general public, and subjects exposed to cancer causing agents (i.e., carcinogens) such as tobacco, asbestos, or other chemical toxins, or a subject who has previously been treated for cancer and is in apparent remission.

The instant methods include isolation of miRNAs from the bodily fluids of the patients. In one aspect of the invention, a miRNA of interest may be detected in a body fluid such as blood, amniotic fluid, cerebrospinal fluid, plasma, milk, semen, serum, sputum, saliva and urine. In one aspect of the instant invention, the miRNA is detected in urine. In another embodiment, the miRNA is detected in serum.

The instant method of the miRNA isolation of the instant invention can utilize commercially available anion exchange materials. Either strong or weak anion exchangers may be employed. By utilizing selected solutions for adsorption and elution, the miRNA can be purified, concentrated, and substantially isolated.

By employing a solution at known ionic strength for the initial binding of the miRNA to the anion exchange column materials, most of the water soluble components including other electronegative molecules such as proteins (weakly-bound contaminants) can be washed through the column. For elution, the required ionic strength is reached by using known concentrations of a salt such as NaCl, which may be mixed with a buffer to control pH, ideally corresponding to the lowest ionic strength at which the nucleic acids will completely elute. Contaminating substances bound to the anion exchange resin with higher stringency than the nucleic acids may thereby be left within the column, i.e., stronger bound contaminants are separated away from the nucleic acids.

A preferred weak exchanger is one in which primary, secondary, or tertiary amine groups (i.e., protonatable amines) provide exchange sites. The strong base anion exchanger has quaternary ammonium groups (i.e., not protonatable and always positively charged) as exchange sites. Both exchangers are selected in relation to their respective absorption and elution ionic strengths and/or pH for the miRNA being separated. The solution strengths are higher than the binding strengths.

In one aspect of the invention, a method is provided for isolation tranrenal miRNA from urine, the method comprising providing urine from a subject; optionally separating cells and cell debris from the urine by filtration or centrifugation; adding EDTA and Tris-HCI to the urine, adding silica free anion exchange resin to urine, incubating the mixture, removing the anion exchange medium from the urine, and eluting miRNA from the resin.

In one embodiment of the method of isolating miRNA from urine, the concentration of EDTA and Tris-HCI after it is added to the urine is in a range of 10-100 mM, and the pH of the solution is between about 8.0 and about 8.5.

In a further embodiment, the body fluid is optionally pre-filtered through a membrane prior to adsorption onto the anion-exchange medium.

In a further embodiment, the anion exchange medium is a sepharose-based resin functionalized with cationic quaternary ammonium groups. Examples of sepharose-based resins, functionalized with cationic ammonium groups include Q-Sepharose™ ANX-4 Sepharose™ Fast Flow, DEAE-Sepharose™, and Q-Sepharose-XL™ DEAE Sepharose Fast Flow (GE Healthcare).

In a further embodiment, the anion exchange medium is selected from sepharose-based quaternary ammonium anion exchange medium such as Q-filters or Q-resin.

In yet another embodiment, the application of the instant method may be extended to monitoring pharmacokinetics of synthetic siRNA in the patient's urine to enhance optimization of the siRNA drug design.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

EXAMPLES

The examples are presented in order to more fully illustrate the various embodiments of the invention. These examples should in no way be construed as limiting the scope of the invention recited in the appended claims.

Example 1

Extraction of miRNA from Urine:

Urine Collection:

For these experiments, urine specimens from patients or volunteers were collected in a sterile 110 ml urine collection cup and were immediately supplemented with EDTA up to final concentration between 10 and 150 mM, preferably 50 mM. Specimens were stored in 10-50 ml aliquots at −80° C. Optional filtration of urine was carried out on Stericup™ (Millipore, Vacuum Driven Filtration System, 0.45µ Durapore™ filter) immediately after specimen collection before the EDTA was added.

Q Binding:

In a 50 ml tube 20 mL of urine was diluted with equal volume of 50 mM EDTA (pH 8.0) and 50 mM Tris-HCl (pH 8.0) which was then supplemented with 1-2 ml of Q-Sepharose™ (GE Healthcare; 17-0510-10) slurry and rigorously mixed 10-30 min at room temperature. The resin, with bound nucleic acids, was collected by centrifugation at 2000 g for 5 minutes at room temperature in a table top clinical centrifuge using a swing bucket rotor. All but ~500 µl of supernatant was removed by aspiration. The resin pellet was resuspended in the remaining supernatant and transferred to a Micro Bio-Spin Chromatography Column (Bio-Rad) or equivalent, which was operated either by centrifugation of vacuum. The resin in the column was washed three times with 500 µl 2×SSC (300 mM NaCL/30 mM sodium citrate (pH 7.0)) or with buffer with comparable ionic strength (e.g. 300 mM NaCl or LiCl). Nucleic acids can be eluted from Q-Sepharose with high ionic strength (e.g 1M NaCl or LiCl) but the methods described below preserves RNA better.

Elution from O-Sepharose™ and TRIzol™ Phase Separation:

Bound nucleic acids were further eluted with 500 µl of TRIzol™ reagent (Invitrogen). The extraction of nucleic acids from TRIzol was carried out according manufacturer's recommendations. Briefly, for phase separation TRIzol eluate was supplemented with 100 µl chloroform, mixed vigorously, incubated at room temperature for 3-5 minutes and centrifuged at 12,000×g for 15 min at 4° C. While avoiding touching the interphase, 300 µl of the upper phase was transferred into a fresh centrifuge tube. Then the nucleic acids were precipitated or additionally cleaned and desalted on a silica column.

Nucleic Acid Precipitation:

For nucleic acid precipitation, the above described preparation was supplemented with 1 µl of 20 mg/mL glycogen (Roche) and 300 µl of 100% isopropyl alcohol. Nucleic acids were collected by centrifugation, the pellet was washed twice with 200 µl of 70% ethanol, allowed to air dry for 5 min at room temperature, and then the nucleic acids were dissolved in 30 µl of 0.1 mM EDTA/1×RNA Secure (Ambion). The samples were incubated at 60° C. for 10 min to inactivate any residual RNase activity.

Silica Column Cleaning of Nucleic Acids:

For binding to a silica column (Qiagen PCR clean columns or equivalent) 3 volumes of 96% ethanol were added to nucleic acid preparation from the TRIzol upper phase, and, after 3 minutes incubation at room temperature, the mixture was loaded onto the column. The column was washed twice with 500 µl 2 M LiCl/80% ethanol and twice with 500 µl 80% ethanol. Nucleic acids were eluted with 50 µl of 0.1 mM EDTA/1×RNA Secure (Ambion). The samples were incubated at 60° C. for 10 min to inactivate any residual RNase.

DNase I and RNase A Digestion:

To verify the nucleic acid identity of the material extracted from urine with the above described protocol, the instant prep was digested with DNase I and/or RNase A. DNase I digestion was carried out in the DNase I Reaction Buffer (NEB) containing 2 units of RNase free DNase I (NEB). RNase A digestion was performed in TE buffer supplemented with 50 ng/mL boiled RNase A. Samples were incubated at 37° C. for 60 min and after addition of loading dye samples were subjected to electrophoresis on 5% polyacrylamide 1×TBE gels and stained with 1/10000 diluted SYBR® Gold (Invitrogen). As shown in FIG. 1, the isolated material represents low molecular weight nucleic acids, mainly RNA and their fragments. In addition, (see FIG. 1), for comparison nucleic acids from Q-resin were eluted by 3 M NaCl, lanes 2 and 3, and Trizol™, lanes 4 and 5.

In the FIG. 1, lanes 1 and 5, represent nucleic acids isolated with high salt and TriZol elution from Q-Sepharose, respectively; lanes 2 and 6; 3 and 7; 4 and 8, represent nucleic acids after treatment with DNAse, RNAse, or DNAse plus RNAse, respectively.

Also, to demonstrate existence and molecular size of RNA, RNA aliquots of purified nucleic acids were digested with DNaseI, lanes 3 and 5.

Extraction of RNA from Serum

For these experiments, 1.2 ml of TRIzol LS were added to 0.4 ml of serum, and the mixture was centrifuged 10 at 14,000 rpm. The supernatant was transferred into a 2 ml Eppendorf tube, 0.3 ml of chloroform was added, and the mixture was shaken for 15 seconds. After centrifugation at 14,000 rpm for 15 min, the supernatant was transferred into a 5 ml tube and ethanol was added up to final concentration of 70%. The mixture was loaded on a Quiagen Quick column on a vacuum manifold, and the column was washed twice with 0.5 ml of 2M LiCl-80% EtOH, once with 0.5 ml of 80% ethanol-80 mM sodium acetate (pH 5.0), and finally with 0.5 ml of 95% ethanol. The column was centrifuged in 1.5 ml Eppendorf tube 3 min at 14,000 rpm, and RNA was eluted with 40 µl $H_2O$.

Example 2

This Example demonstrates that miRNA, from dying cells, cross the kidney barrier and may be detected in the urine of a patient.

Detection of Human miRNA Molecules in Urine

Micro RNA species that were analyzed in this example can be grouped in three distinct types, namely ubiquitous miRNAs, which are expressed in all or multiple tissues, tissue-specific miRNAs, and miRNAs in which expression is significantly altered in a particular tissue or cell type. As shown by Table 1, 20 different miRNAs were obtained from urine of 16 healthy volunteers and enrolled donors and later detected by real time RT-PCR using commercially available miRNA expression analysis kit (ABI). Corresponding synthetic miRNA oligonucleotides were used as standards. Reactions were carried out strictly as recommended by the supplier.

TABLE 1

Detected miRNA

| SEQ ID NO: | ID | Sequence | Expression |
|---|---|---|---|
| 1 | hsa-miR-127 | UCGGAUCCGUCUGAGCUUGGCU | Brain overexpressed |
| 2 | hsa-miR-153 | UUGCAUAGUCACAAAAGUGA | Brain overexpressed |
| 3 | hsa-miR-129 | CUUUUUGCGGUCUGGGCUUGC | Brain-specific |
| 4 | hsa-miR-137 | UAUUGCUUAAGAAUACGCGUAG | Brain overexpressed |
| 5 | hsa-miR-218 | UUGUGCUUGAUCUAACCAUGU | Ubiquitous, Brain overexpressed |
| 6 | hsa-miR-219 | UGAUUGUCCAAACGCAAUUCU | Brain-specific |
| 7 | hsa-miR-128a | UCACAGUGAACCGGUCUCUUUU | Brain-specific |
| 8 | hsa-miR-9 | UCUUUGGUUAUCUAGCUGUAUGA | Brain overexpressed |
| 9 | hsa-miR-138 | AGCUGGUGUUGUGAAUC | Brain, Thyroid |
| 10 | hsa-miR-134 | UGUGACUGGUUGACCAGAGGG | Brain and several other tissues |
| 11 | hsa-miR-124a | UUAAGGCACGCGGUGAAUGCCA | Brain-specific |
| 12 | hsa-miR-122a | UGGAGUGUGACAAUGGUGUUUGU | Liver-specific |
| 13 | hsa-miR-133a | UUGGUCCCCUUCAACCAGCUGU | Heart and Muscle overexpressed |
| 14 | hsa-miR-1 | UGGAAUGUAAAGAAGUAUGUA | Heart and Muscle overexpressed |
| 15 | hsa-miR-335 | UCAAGAGCAAUAACGAAAAAUGU | Ubiquitous |
| 16 | hsa-miR-16 | UAGCAGCACGUAAAUAUUGGCG | Ubiquitous |
| 17 | hsa-miR-215 | AUGACCUAUGAAUUGACAGAC | Small intestine and colon overexpressed |
| 18 | hsa-miR-135b | UAUGGCUUUUCAUUCCUAUGUG | Placenta-overexpressed |

TABLE 1-continued

Detected miRNA

| SEQ ID NO: | ID | Sequence | Expression |
|---|---|---|---|
| 19 | hsa-miR-517c | AUCGUGCAUCCUUUUAGAGUGU | Placenta-overexpressed |
| 20 | hsa-miR-518e | AAAGCGCUUCCCUUCAGAGUGU | Placenta-overexpressed |

All three types of miRNA were detected in most preps of urinary RNA. The highest copy numbers were characteristic of ubiquitous miRNA. However, tissue-specific miRNA or miRNA over-expressed in a particular tissue or cell type were also detectable. It has been unequivocally demonstrated that a portion of miRNA from dying cells is not degraded but appears in the bloodstream and is finally excreted into urine.

Example 3

The Example demonstrates that miRNA from human nasopharyngeal carcinoma (NPC) cells can cross the patient's kidney barrier and can be detected in patient's urine by real time RT-PCR.

Virus-Derived miRNA in Urine

It is known that some viruses also encode and produce miRNAs. Since Epstein-Barr virus (EBV) is involved in development of human nasopharyngeal carcinoma (NPC), instant system was used to find out if viral miRNA from NPC cells can reach patient's urine and be detected there. Urine samples from NPC patients were collected and stored according to the procedures described in the Example 1 of this application. EBV infection was confirmed by the detection of virus-specific DNA sequences in urine. Urine collected from healthy donor was negative for EBV specific DNA sequences. A two EBV-specific miRNAs BART3-3p and BART1-3p were analyzed in this study:

```
                                     SEQ ID NO: 21
BART3-3P    CGC ACC ACU AGU CAC CAG GUG U

SEQ ID NO: 22
BART1-3P    UAG CAC CGC UAU CCA CUA UGU CU
```

Reverse transcription was performed in 15 one tenth of the RT reaction was subjected to PCR amplification using Jump-Start DNA polymerase from Sigma. The following primers were used at 500 nM concentration:

```
                                     (SEQ ID NO: 23)
BART3-3PRT   GTC GTA TCC AGT GCA GGG TCC GAG GTA
             TTC GCA CTG GAT ACG ACA CAC CT (SEQ ID NO: 24)
BART1-3PRT   GTC GTA TCC AGT GCA GGG TCC GAG GTA
             TTC GCA CTG GAT ACG ACA GAC AT (SEQ ID NO: 25)
BART3-3PF    CGC CGC ACC ACT AGT CAC (SEQ ID NO: 26)
BART1-3PF    CGC TAG CAC CGC TAT CCA (SEQ ID NO: 27)
miRNACR      GTG CAG GGT CCG AGG T
```

Products were analyzed in 15% polyacrylamide gel (PAAG).

Figure 2:
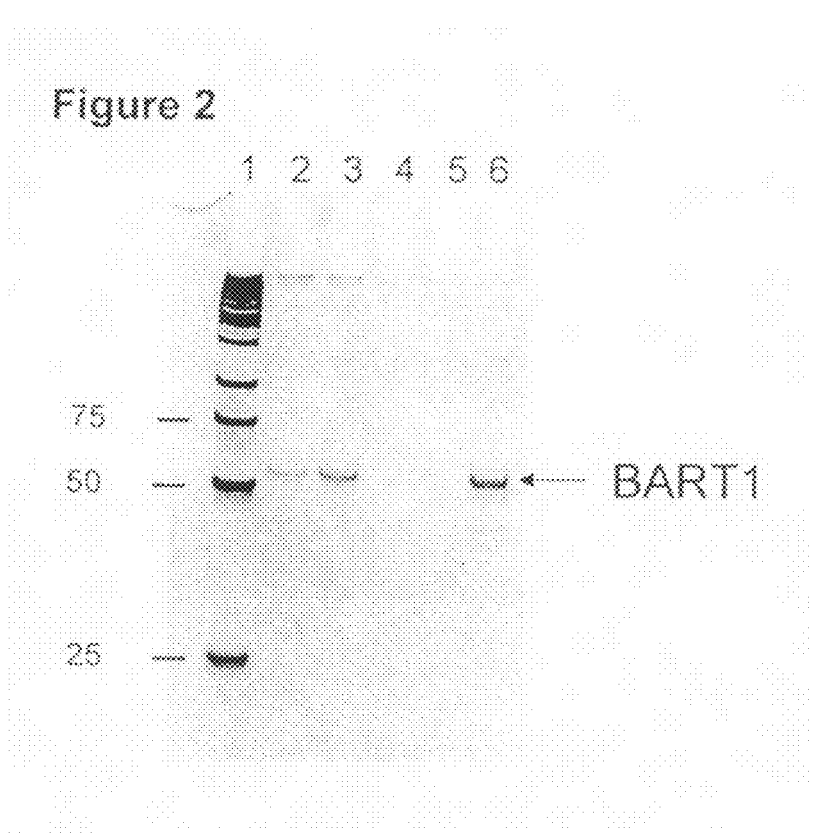
FIG. 2 is a photograph of a polyacrylamide gel analysis of EBV derived BART1 miRNA specific RT-PCR product.
Figure 3:
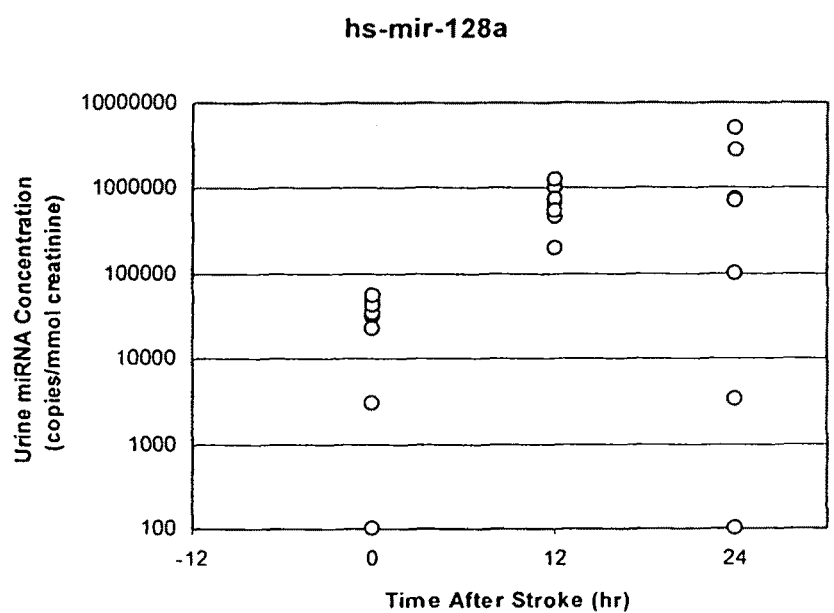
FIGS. 3A to 3G are dot plot representations of the normalized concentrations of miRNA in urine samples of patients at 12 and 24 hour time points after brain stroke.

As demonstrated by FIG. 2, both BART3 and BART 1 miRNA species were detected in urine from NPC patients but not in the urine sample from a healthy donor. These data again indicate that miRNA from dying cells located outside of urinary system can be detected in the urine. In the FIG. 2, lane 1, represents markers; lanes 2 and 3, represent patients with nasopharyngeal carcinoma, lanes 4 and 5, represent control patients, and lane 6, represents positive control, which represents respective synthetic miRNAs.

Example 4

This example demonstrates that the neuronal death caused by stroke can be registered in vivo by measurements of the concentrations of neuron-specific miRNA in the patient's urine.

Brain Stroke Diagnosis

For these experiments, patients with brain stroke were investigated for analysis of changes in concentrations of brain-specific miRNA or miRNA which are over-expressed in brain, after stroke. Since currently it is not known in what brain cell types and in what brain areas these miRNA are expressed, 9 different brain specific miRNA were studied.

Patients:

Urine samples were collected from patients accepted at a hospital through the emergency room. Diagnosis of brain stroke was based on clinical symptoms. Urine samples were collected at 12 and 24 hours after the stroke. Control urine samples were donated by age matched volunteers but without stroke symptoms. Samples were collected and stored according to the procedures described in the Example 1 of this application.

miRNA Species:

miRNA from urine was extracted according to the procedure described in the Example 1. An amount of RNA equivalent to that isolated from 675 µl of urine underwent reverse transcription PCR and 1/10 of the RT-PCR mixture underwent final real time PCR, which was carried out using the protocol provided by the manufacturer. Data obtained were normalized for individual kidney filtration rates by re-calculation per creatinine concentration in urine. For these experiments, urine samples collected from healthy donors from same age group were used as baseline. Different miRNA species are presented as follows:

A. hsa-mir-128a
B. hsa-mir-9
C. hsa-mir-127
D. hsa-mir-137
E. hsa-mir-129
F. hsa-mir-219
G. hsa-mir-218

Results summarized in FIGS. 3A to 3G clearly demonstrate that after brain stroke, there is a significant increase in the levels of several brain specific miRNA (128a, 129, 218, 219)—reflecting kinetics of the brain cell death.

Example 5

This example demonstrates that kinetics of the miRNA concentrations in patient's urine after stroke provides information about disease outcome.
Brain Stroke Monitoring For the experiments, patients with brain stroke were investigated for analysis of correlation between changes in concentrations of brain-specific miRNA and disease development.
Patients:

Urine samples were collected from patients accepted at a hospital through the emergency room. Diagnosis of brain stroke was based on clinical symptoms and MRI analysis. Urine samples were collected at 12, 24, 48 hours and a week after the stroke. Patient clinical status was evaluated 30 days after stroke. Control urine samples were donated by age matched volunteers but without stroke symptoms. Samples were collected and stored according to the procedures described in the Example 1 of this application.
miRNA Species:

miRNA from urine was extracted according to the procedure described in Example 1 and analyzed with TaqMan miRNA assays (Applied Biosystems). An amount of RNA equivalent to that isolated from 400 µl of urine underwent reverse transcription PCR and 1/10 of the RT-PCR mixture underwent final real time PCR, which was carried out using the protocol provided by the manufacturer. Data obtained were normalized for individual kidney filtration rates by re-calculation per creatinine concentration in urine. For these experiments, urine samples collected from healthy donors from same age group were used as baseline.

Figure 4:
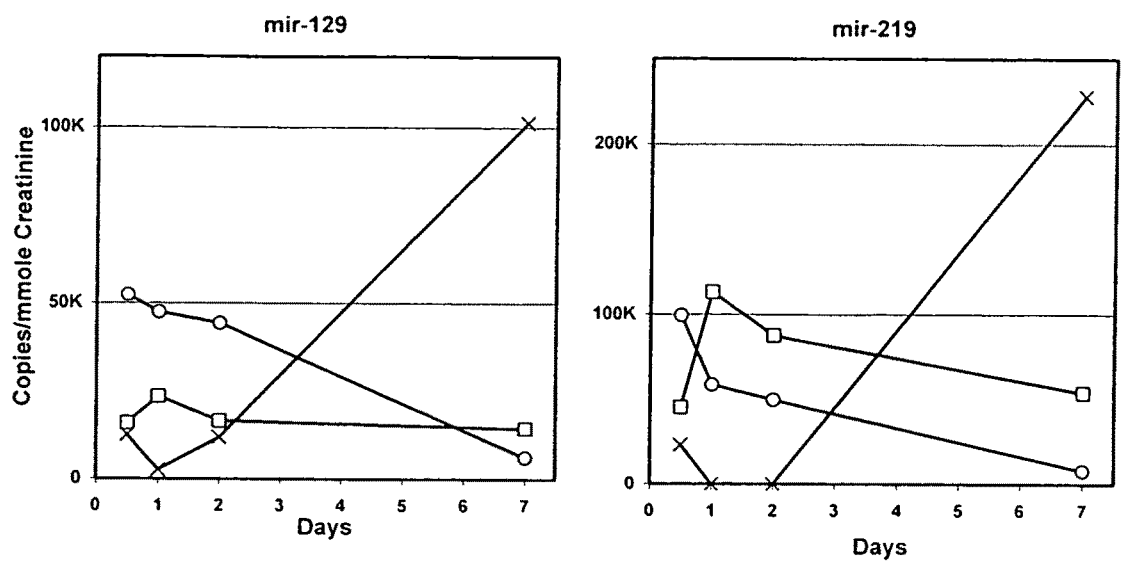
FIG. 4 is a diagram representing correlation between changes in miRNAs 129 and 219 concentrations and brain stroke outcome. The patients labeled as ○ and □ improved their clinical status a month after stroke, and the clinical status of the patient labeled x has deteriorated a month after a stroke.

Results summarized in FIGS. 4A and B clearly demonstrate that the dynamics of changes in Tr-miRNA 129 and Tr-miRNA 219 after brain stroke are different in different patients and correlates with the disease development. The increase in neuronal death a week after stroke in patient #3 corresponds to worsening in the patient clinical status. At the same time two patients, whose transrenal neuron-specific miRNA had tendency to normalization, demonstrated significant improvement.

Example 6

Alzheimer's Disease Diagnosis

Alzheimer's disease is a progressive neurological disease that is caused by the death of neurons, particularly in the cortex and hippocampus. The diagnosis is based on neurological examination and the exclusion of other causes of dementia whereas the definitive diagnosis can be made only at autopsy. The instant invention demonstrates that excessive neuronal death characterizing Alzheimer's disease may be monitored by measuring levels of specific brain miRNAs isolated from the patient's urine.

For these experiments, patients diagnosed with Alzheimer's disease were investigated for analysis of changes in concentrations of brain-specific or over-expressed miRNA as a result of neuronal death.

Patients:

Urine and serum samples were collected from patients diagnosed with various stages of the Alzheimer's disease. Control urine and serum samples were donated by age matched volunteers but without symptoms of Alzheimer's disease. Samples were collected and stored according to the procedures described in the Example 1 of this application. Some urine samples were filtered after collection as described in Example 1 to delete cells and cell debris.
miRNA Species:

RNA from urine and serum was extracted according to the procedures described in the Example 1.

In one set of experiments an amount of RNA equivalent to that isolated from 750 µl of urine underwent reverse transcription PCR and 1/10 of the RT-PCR mixture underwent final real time PCR, which was carried out using the protocol provided by the manufacturer (Applied Biosystems). Data obtained were normalized for individual kidney filtration rates by re-calculation per creatinine concentration in urine. FIG. 5 clearly demonstrates that concentrations of several brain specific miRNAs is increased in the urine of Alzheimer's patients.

In another set of experiments, RNA isolated from filtered urine or serum was analyzed. An amount of RNA equivalent to that isolated from 0.6 ml of urine or 50 µl of serum underwent reverse transcription PCR and 1/10 of the RT-PCR mixture underwent final real time PCR, which was carried out using the protocol provided by the manufacturer (Applied Biosystems). Data obtained for urinary miRNA were normalized for individual kidney filtration rates by re-calculation per creatinine concentration in urine. Data obtained for plasma miRNA were normalized per ubiquitous miRNA-16. FIGS. 6 and 7 show that the levels of some neuron-specific miRNAs are higher in both filtered urine and serum of the Alzheimer's patients compared to age-matched controls.

Example 7

Parkinson's Disease

Parkinson's disease is a degenerative disorder of the central nervous system that often impairs the sufferer's motor skills and speech. The instant invention demonstrates that excessive cellular death of dopaminergic neurons, characterizing Parkinson's disease may be monitored by measuring levels of specific brain miRNAs isolated from the patient's urine.

For these experiments, patients diagnosed with Parkinson's were investigated for analysis of changes in concentrations of brain-specific miRNA or over-expressed miRNA as a result of neuronal death.

Patients.

Urine samples were collected from patients diagnosed with various stages of the Parkinson's disease. Control urine samples were donated by age matched volunteers without symptoms of Parkinson's disease. Samples were collected and stored according to the procedures described in the Example 1 of this application.

miRNA Species.

For these experiments, RNA from urine was extracted according to the procedure described in the Example 1. Amount of RNA equivalent to that isolated from 750 µl of urine underwent reverse transcription PCR and 1/10 of the RT-PCR mixture underwent final real time PCR, which was carried out using the protocol provided by the manufacturer (Applied Biosystems). Data obtained were normalized for individual kidney filtration rates by re-calculation per creatinine concentration in urine. FIG. 8 demonstrates that concentrations of several brain specific miRNAs is increased in the urine of the patients with Parkinson disease.

Example 8

Prenatal Testing for Pregnancy-Related or Fetal Diseases

The principal finding of permeability of the kidney barrier for miRNA molecules opens the way for the use of maternal urine to perform completely noninvasive prenatal diagnosis of congenital diseases. One can perform such a noninvasive screen as follows.

First, a sample of urine is gathered from a pregnant patient. Where desired, miRNA in the urine sample is then be isolated, purified and/or treated to prevent degradation using methods described above. MiRNA profiling is then performed using quantitative PCR or miRNA array and the data obtained are used to determine different fetal pathologies, as described for other pathologies above.

Example 9

Down Syndrome

For the experiments, differences in concentrations of brain-specific miRNA in maternal urine between women pregnant with normal and Down syndrome fetuses were investigated.

Figure 9:
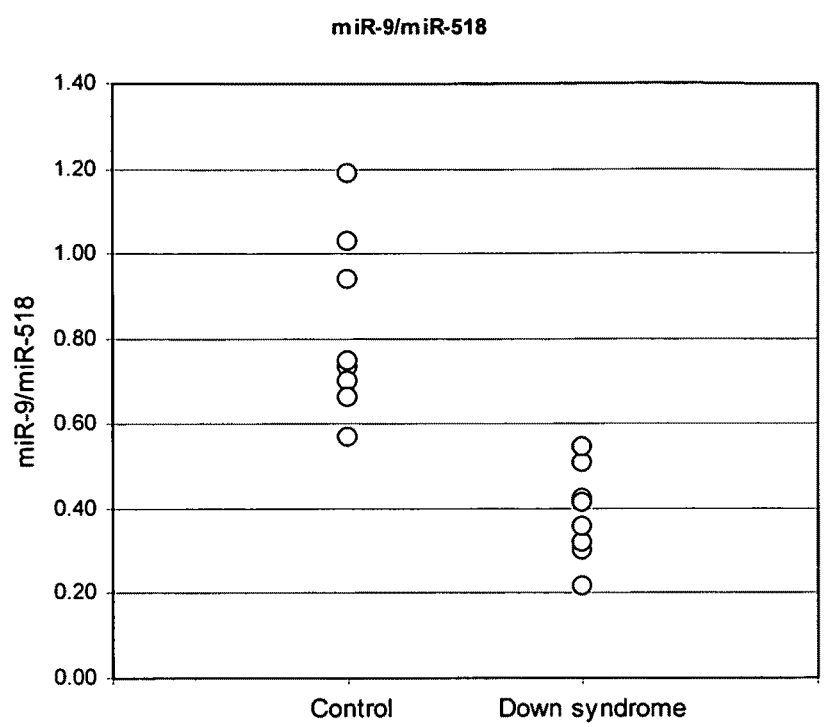
FIG. 9 is a dot plot representation of the normalized concentration of miRNA-9 in urine samples of women pregnant with Down syndrome and normal fetuses.

Patients:

Urine samples were collected from pregnant women diagnosed with Down syndrome by amniocentesis. Control urine samples were donated by age matched women with normal pregnancies. Samples were collected and stored according to the procedures described in the Example 1 of this application.

miRNA Species:

miRNA from urine was extracted according to the procedure described in the Example 1. An amount of RNA equivalent to that isolated from 750 µl of urine underwent reverse transcription PCR and 1/10 of the RT-PCR mixture underwent final real time PCR, which was carried out using the protocol provided by the manufacturer. Data obtained were normalized per placenta-specific miRNA 518. FIG. 9 demonstrates lower concentration the brain-specific miRNA 9 in urine of women pregnant with Down syndrome fetuses compared to urine of women with normal pregnancies, which indicates insufficient cell death compared to respective controls.

The invention claimed is:

1. A method of detecting at least one cell-free miRNA released from at least one cell in a subject, the method comprising:
   a) obtaining a sample of a body fluid, selected from urine or blood, from a subject;
   b) separating a soluble fraction of said sample of urine or blood;
   c) detecting and quantitating at least one cell-free miRNA in the soluble fraction with at least one oligonucleotide primer or probe that is substantially complementary to a part of said at least one cell-free miRNA.

2. The method of claim 1, wherein said at least one cell-free miRNA is selected from SEQ ID NOs: 1-7, 9, 10, 13-15, and 17-20.

3. The method of claim 1 wherein said body fluid is urine.

4. The method of claim 3, wherein said detecting and quantitating step is performed by a method selected from the group consisting of hybridization, cycling probe reaction, polymerase chain reaction, nested polymerase chain reaction, PCR to analyze single strand conformation polymorphisms, and ligase chain reaction.

5. The method of claim 3, wherein said urine is further treated to reduce nucleic acid degradation.

6. The method of claim 5, wherein reducing nucleic acid degradation comprises inhibiting nuclease activity by addition of RNase inhibitor(s), heat inactivation, or by treating said urine sample with a compound selected from the group consisting of: guanidine-HCl, guanidine isothiocyanate, N-lauroylsarcosine, and sodium dodecylsulphate.

7. The method of claim 3, wherein said urine sample has been held in the bladder less than 12 hours.

8. The method of claim 1, wherein said body fluid is blood and said soluble fraction is serum.

9. The method of claim 8, wherein said detecting and quantitating step includes a technique selected from the group consisting of hybridization, cycling probe reaction, polymerase chain reaction, nested polymerase chain reaction, PCR to analyze single strand conformation polymorphisms, and ligase chain reaction.

10. The method of claim 1, wherein the at least one cell-free miRNA is from a pathogen and the method comprises determining the presence of a pathogen infection.

11. The method of claim 10, wherein said pathogen is a virus.

12. The method of claim 11, wherein said virus is Epstein-Barr virus.

13. The method of claim 1, wherein said cell-free miRNA is brain specific.

14. The method of claim 1, wherein said subject is pregnant and said at least one cell-free miRNA is released by a fetal cell in the subject.

15. A method of monitoring the level of at least one cell-free miRNA released from at least one cell in a subject, the method comprising:
   a) detecting and quantitating at least one cell-free miRNA according to the method of claim 1 in a first sample of body fluid selected from urine or blood from a subject at a first period of time;
   b) detecting and quantitating the same cell-free miRNA according to the method of claim 1 in a second sample of the same body fluid from the subject at a second period of time; and
   c) comparing the level of said cell-free miRNA from said first period of time to the level of said cell-free miRNA from said second period of time.

16. The method of claim 15 wherein said body fluid is urine.

17. The method of claim 15 wherein said body fluid is blood.

* * * * *